(12) United States Patent
Tamarkin et al.

(10) Patent No.: US 8,362,091 B2
(45) Date of Patent: *Jan. 29, 2013

(54) FOAMABLE VEHICLE AND PHARMACEUTICAL COMPOSITIONS THEREOF

(75) Inventors: Dov Tamarkin, Maccabim (IL); Doron Friedman, Karmei Yosef (IL); Meir Eini, Ness Ziona (IL); Alex Besonov, Rehovot (IL)

(73) Assignee: Foamix Ltd., Rehovot (IL)

( * ) Notice: Subject to any disclaimer, the term of this patent is extended or adjusted under 35 U.S.C. 154(b) by 135 days.

This patent is subject to a terminal disclaimer.

(21) Appl. No.: 12/767,511

(22) Filed: Apr. 26, 2010

(65) Prior Publication Data

US 2010/0266510 A1    Oct. 21, 2010

Related U.S. Application Data

(63) Continuation of application No. 11/430,599, filed on May 9, 2006, now Pat. No. 7,704,518, which is a continuation-in-part of application No. 10/835,505, filed on Apr. 28, 2004, now Pat. No. 7,820,145.

(60) Provisional application No. 60/492,385, filed on Aug. 4, 2003, provisional application No. 60/530,015, filed on Dec. 16, 2003, provisional application No. 60/679,020, filed on May 9, 2005, provisional application No. 60/784,793, filed on Mar. 21, 2006.

(51) Int. Cl.
*A01N 25/16* (2006.01)
*A61K 47/00* (2006.01)
*A61K 47/30* (2006.01)
*A61K 47/32* (2006.01)

(52) U.S. Cl. ........... 514/945; 424/405; 514/772.2; 514/772.3; 514/772.6; 514/776; 514/778

(58) Field of Classification Search .......... None
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brighttenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,867 A | 8/1966 | Lehmann |
| 3,263,869 A | 8/1966 | Corsette |
| 3,298,919 A | 1/1967 | Charles et al. |
| 3,301,444 A | 1/1967 | Wittke |
| 3,303,970 A | 2/1967 | Breslau et al. |
| 3,330,730 A | 7/1967 | Hernaadez |
| 3,333,333 A | 8/1967 | Noack |
| 3,346,451 A | 10/1967 | Collins et al. |
| 3,366,494 A | 1/1968 | Bower |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borocki |
| 3,563,098 A | 2/1971 | Weber, III |

(Continued)

FOREIGN PATENT DOCUMENTS

| AU | 198780257 | 9/1986 |
|---|---|---|
| CA | 2422244 | 9/2003 |

(Continued)

OTHER PUBLICATIONS

Alcohol SDA 40B,http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Poltethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2006, 6 pages.

(Continued)

*Primary Examiner* — Ernst Arnold
(74) *Attorney, Agent, or Firm* — Fish & Richardson P.C.

(57) ABSTRACT

A hygroscopic pharmaceutical composition includes at least one hygroscopic substance at a concentration sufficient to provide an Aw value of at least 0.9 and an antiinfective agent. A foamble pharmaceutical carrier includes about 50% to about 98% of a polar solvent selected from the group consisting of a polyol and PEG; 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

18 Claims, 1 Drawing Sheet

U.S. PATENT DOCUMENTS

| | | |
|---|---|---|
| 3,574,821 A | 4/1971 | Pfirrmann et al. |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves et al. |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |

| | | | | | |
|---|---|---|---|---|---|
| 5,133,972 A | 7/1992 | Ferrini et al. | 5,613,623 A | 3/1997 | Hildebrandt |
| 5,135,915 A | 8/1992 | Czarniecki et al. | 5,614,171 A | 3/1997 | Clavenna et al. |
| 5,137,714 A | 8/1992 | Scott | 5,614,178 A | 3/1997 | Bloom et al. |
| 5,143,717 A | 9/1992 | Davis | 5,635,469 A | 6/1997 | Fowler et al. |
| 5,156,765 A | 10/1992 | Smrt | 5,641,480 A | 6/1997 | Vermeer |
| 5,164,357 A | 11/1992 | Bartman et al. | 5,643,600 A | 7/1997 | Mathur |
| 5,164,367 A | 11/1992 | Pickart | 5,645,842 A | 7/1997 | Gruning et al. |
| 5,167,950 A | 12/1992 | Lins | 5,650,554 A | 7/1997 | Moloney |
| 5,171,577 A | 12/1992 | Griat et al. | 5,658,575 A | 8/1997 | Ribier et al. |
| 5,196,405 A | 3/1993 | Packman | 5,658,749 A | 8/1997 | Thornton |
| 5,204,093 A | 4/1993 | Victor | 5,658,956 A | 8/1997 | Martin et al. |
| 5,208,031 A | 5/1993 | Kelly | 5,663,208 A | 9/1997 | Martin |
| 5,217,707 A | 6/1993 | Szabo et al. | 5,672,634 A | 9/1997 | Tseng et al. |
| 5,219,877 A | 6/1993 | Shah et al. | 5,679,324 A | 10/1997 | Lisboa et al. |
| 5,221,696 A | 6/1993 | Ke et al. | 5,683,710 A | 11/1997 | Akemi et al. |
| 5,230,897 A | 7/1993 | Griffin et al. | 5,686,088 A | 11/1997 | Mitra et al. |
| 5,236,707 A | 8/1993 | Stewart, II | 5,693,258 A | 12/1997 | Tonomura et al. |
| 5,252,246 A | 10/1993 | Ding et al. | 5,695,551 A | 12/1997 | Buckingham et al. |
| 5,254,334 A | 10/1993 | Ramirez et al. | 5,700,396 A | 12/1997 | Suzuki et al. |
| 5,262,407 A | 11/1993 | Leveque et al. | 5,716,611 A | 2/1998 | Oshlack et al. |
| 5,266,592 A | 11/1993 | Grub et al. | 5,716,621 A | 2/1998 | Bello |
| 5,279,819 A | 1/1994 | Hayes | 5,719,122 A | 2/1998 | Chiodini et al. |
| 5,286,475 A | 2/1994 | Louvet et al. | 5,719,197 A | 2/1998 | Kanios et al. |
| 5,300,286 A | 4/1994 | Gee | 5,725,872 A | 3/1998 | Stamm et al. |
| 5,301,841 A | 4/1994 | Fuchs et al. | 5,725,874 A | 3/1998 | Oda |
| 5,308,643 A | 5/1994 | Osipow et al. | 5,730,964 A | 3/1998 | Waldstreicher |
| 5,314,904 A | 5/1994 | Egidio et al. | 5,733,558 A | 3/1998 | Breton et al. |
| 5,322,683 A | 6/1994 | Mackles et al. | 5,733,572 A | 3/1998 | Unger et al. |
| 5,326,557 A | 7/1994 | Glover et al. | 5,747,049 A | 5/1998 | Tominaga |
| 5,344,051 A | 9/1994 | Brown | 5,753,241 A | 5/1998 | Ribier et al. |
| 5,346,135 A | 9/1994 | Vincent | 5,753,245 A | 5/1998 | Fowler et al. |
| 5,352,437 A | 10/1994 | Nakagawa et al. | 5,759,520 A | 6/1998 | Sachetto |
| 5,369,131 A | 11/1994 | Poli et al. | 5,759,579 A | 6/1998 | Singh et al. |
| 5,378,451 A | 1/1995 | Gorman et al. | 5,767,104 A | 6/1998 | Bar-Shalom et al. |
| 5,378,730 A | 1/1995 | Lee et al. | 5,773,410 A | 6/1998 | Yamamoto |
| 5,380,761 A | 1/1995 | Szabo et al. | 5,783,202 A | 7/1998 | Tomlinson et al. |
| 5,384,308 A | 1/1995 | Henkin | 5,788,664 A | 8/1998 | Scalise |
| 5,385,943 A | 1/1995 | Nazzaro-Porro | 5,792,448 A | 8/1998 | Dubief et al. |
| 5,389,676 A | 2/1995 | Michaels | 5,792,922 A | 8/1998 | Moloney et al. |
| 5,397,312 A | 3/1995 | Rademaker et al. | 5,797,955 A | 8/1998 | Walters |
| 5,398,846 A | 3/1995 | Corba et al. | 5,804,546 A | 9/1998 | Hall et al. |
| 5,399,205 A | 3/1995 | Shinohara et al. | 5,817,322 A | 10/1998 | Xu et al. |
| 5,411,992 A | 5/1995 | Eini et al. | 5,824,650 A | 10/1998 | De Lacharriere et al. |
| 5,422,361 A | 6/1995 | Munayyer et al. | 5,833,960 A | 11/1998 | Gers-Barlag et al. |
| 5,429,815 A | 7/1995 | Faryniarz et al. | 5,833,961 A | 11/1998 | Siegfried et al. |
| 5,435,996 A | 7/1995 | Glover et al. | 5,837,270 A | 11/1998 | Burgess |
| 5,447,725 A | 9/1995 | Damani et al. | 5,840,744 A | 11/1998 | Borgman |
| 5,449,520 A | 9/1995 | Frigerio et al. | 5,840,771 A | 11/1998 | Oldham et al. |
| 5,451,404 A | 9/1995 | Furman | 5,843,411 A | 12/1998 | Hernandez et al. |
| 5,482,965 A | 1/1996 | Rajadhyaksha | 5,846,983 A | 12/1998 | Sandborn et al. |
| 5,491,245 A | 2/1996 | Gruning et al. | 5,849,042 A | 12/1998 | Lim et al. |
| 5,500,211 A | 3/1996 | George et al. | 5,856,452 A | 1/1999 | Moloney et al. |
| 5,508,033 A | 4/1996 | Briand et al. | 5,858,371 A | 1/1999 | Singh et al. |
| 5,512,555 A | 4/1996 | Waldstreicher | 5,865,347 A | 2/1999 | Welschoff |
| 5,514,367 A | 5/1996 | Lentini et al. | 5,866,040 A | 2/1999 | Nakama et al. |
| 5,514,369 A | 5/1996 | Salka et al. | 5,869,529 A | 2/1999 | Sintov et al. |
| 5,520,918 A | 5/1996 | Smith | 5,871,720 A | 2/1999 | Gutierrez et al. |
| 5,523,078 A | 6/1996 | Baylin | 5,877,216 A | 3/1999 | Place et al. |
| 5,527,534 A | 6/1996 | Myhling | 5,879,469 A | 3/1999 | Avram et al. |
| 5,527,822 A | 6/1996 | Scheiner | 5,881,493 A | 3/1999 | Restive |
| 5,529,770 A | 6/1996 | McKinzie et al. | 5,885,581 A | 3/1999 | Massand |
| 5,531,703 A | 7/1996 | Skwarek et al. | 5,889,028 A | 3/1999 | Sandborn et al. |
| 5,534,261 A | 7/1996 | Rodgers et al. | 5,889,054 A | 3/1999 | Yu et al. |
| 5,536,743 A | 7/1996 | Borgman | 5,891,458 A | 4/1999 | Britton et al. |
| 5,540,853 A | 7/1996 | Trinh et al. | 5,902,574 A | 5/1999 | Stoner et al. |
| 5,545,401 A | 8/1996 | Shanbrom | 5,902,789 A | 5/1999 | Stoltz |
| 5,567,420 A | 10/1996 | McEleney et al. | 5,905,092 A | 5/1999 | Osborne et al. |
| 5,576,016 A | 11/1996 | Amselem et al. | 5,910,382 A | 6/1999 | Goodenough et al. |
| 5,578,315 A | 11/1996 | Chien et al. | 5,911,981 A | 6/1999 | Dahms et al. |
| 5,585,104 A | 12/1996 | Ha et al. | 5,912,007 A | 6/1999 | Pan et al. |
| 5,589,157 A | 12/1996 | Hatfield | 5,914,122 A | 6/1999 | Otterbeck et al. |
| 5,589,515 A | 12/1996 | Suzuki et al. | 5,914,310 A | 6/1999 | Li et al. |
| 5,597,560 A | 1/1997 | Bergamini et al. | 5,922,331 A | 7/1999 | Mausner |
| 5,603,940 A | 2/1997 | Candau et al. | 5,925,669 A | 7/1999 | Katz et al. |
| 5,605,679 A | 2/1997 | Hansenne et al. | 5,948,682 A | 9/1999 | Moloney |
| 5,608,119 A | 3/1997 | Amano et al. | 5,951,544 A | 9/1999 | Konwitz |
| 5,611,463 A | 3/1997 | Favre | 5,951,989 A | 9/1999 | Heymann |
| 5,612,056 A | 3/1997 | Jenner et al. | 5,951,993 A | 9/1999 | Scholz et al. |
| 5,613,583 A | 3/1997 | Kono et al. | 5,952,373 A | 9/1999 | Lanzendorfer et al. |

| | | |
|---|---|---|
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang et al. |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy et al. |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |

| | | |
|---|---|---|
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,820,145 B2 | 10/2010 | Tamarkin et al. |
| 7,960,416 B2 | 6/2011 | Sato et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |

| | | |
|---|---|---|
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0017696 A1 | 1/2007 | Lin et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0156507 A1 | 10/1985 |
| EP | 0186453 | 7/1986 |
| EP | 211550 | 2/1987 |
| EP | 0214865 A2 | 3/1987 |
| EP | 0 216 856 | 4/1987 |
| EP | 0270316 | 6/1988 |
| EP | 297436 | 1/1989 |
| EP | 0 326 196 | 8/1989 |
| EP | 0 336 812 | 10/1989 |
| EP | 0 391 124 | 10/1990 |
| EP | 0404376 | 12/1990 |
| EP | 414920 | 3/1991 |
| EP | 0 485 299 | 5/1992 |
| EP | 0484530 A1 | 5/1992 |
| EP | 0488089 A1 | 6/1992 |
| EP | 0 504 301 | 9/1992 |
| EP | 0 528 190 | 2/1993 |
| EP | 0535327 | 4/1993 |
| EP | 0 552 612 | 7/1993 |
| EP | 0569773 A2 | 11/1993 |
| EP | 0598412 | 11/1993 |
| EP | 0 662 431 | 7/1995 |
| EP | 0676198 | 10/1995 |
| EP | 0738516 | 10/1996 |
| EP | 0 757 959 | 2/1997 |
| EP | 0824911 | 2/1998 |
| EP | 0 829 259 | 3/1998 |
| EP | 0 928 608 | 7/1999 |
| EP | 0979654 A1 | 2/2000 |
| EP | 0993827 A1 | 4/2000 |
| EP | 1 025 836 | 8/2000 |
| EP | 1055425 A2 | 11/2000 |
| EP | 0 506 197 | 7/2001 |
| EP | 1215258 | 6/2002 |
| EP | 1287813 | 3/2003 |
| EP | 1 308 169 | 5/2003 |
| EP | 1 375 386 | 1/2004 |
| EP | 1428521 | 6/2004 |
| EP | 1438946 | 7/2004 |
| EP | 1189579 | 9/2004 |
| EP | 1475381 | 11/2004 |
| EP | 1 483 001 | 12/2004 |
| EP | 1500385 | 1/2005 |
| EP | 1 537 916 | 6/2005 |
| EP | 1 600 185 | 11/2005 |
| EP | 1 670 698 | 6/2006 |
| EP | 1 734 927 | 12/2006 |
| EP | 1 758 547 | 3/2007 |
| EP | 1584324 | 11/2007 |
| EP | 1 889 609 | 2/2008 |
| FR | 2 591 331 | 6/1987 |
| FR | 2 640 942 | 6/1990 |
| FR | 2 736 824 | 1/1997 |
| FR | 2774595 A | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |

| | | | | | | |
|---|---|---|---|---|---|---|
| FR | 2 860 976 | 4/2005 | | JP | 2001072963 | 3/2001 |
| FR | 2915891 | 11/2008 | | JP | 2002012513 | 1/2002 |
| GB | 808104 | 1/1959 | | JP | 2002047136 | 2/2002 |
| GB | 808105 | 1/1959 | | JP | 2002/524490 | 8/2002 |
| GB | 922930 | 4/1963 | | JP | 2002/302419 | 10/2002 |
| GB | 933486 | 8/1963 | | JP | 2003/012511 | 1/2003 |
| GB | 998 490 | 7/1965 | | JP | 2003055146 | 2/2003 |
| GB | 1026831 | 4/1966 | | JP | 2004/047136 | 2/2004 |
| GB | 1 033 299 | 6/1966 | | JP | 2004/250435 | 9/2004 |
| GB | 1 081 949 | 9/1967 | | JP | 2004/348277 | 12/2004 |
| GB | 1121358 | 7/1968 | | JP | 2005/314323 | 11/2005 |
| GB | 1 162 684 | 8/1969 | | JP | 2005350378 | 12/2005 |
| GB | 1 170 152 | 11/1969 | | JP | 2006008574 | 1/2006 |
| GB | 1 201 918 | 8/1970 | | JP | 2006/036317 | 2/2006 |
| GB | 1 347 950 | 2/1974 | | JP | 2006/103799 | 4/2006 |
| GB | 1 351 761 | 5/1974 | | JP | 2006525145 | 11/2006 |
| GB | 1 351 762 | 5/1974 | | JP | 2007131539 | 5/2007 |
| GB | 1 353 381 | 5/1974 | | JP | 4892282 | 3/2012 |
| GB | 1 376 649 | 12/1974 | | KR | 143232 | 7/1998 |
| GB | 1397285 | 6/1975 | | KR | 2001/003063 | 1/2001 |
| GB | 1 408 036 | 10/1975 | | RU | 2277501 | 6/2006 |
| GB | 1 457 671 | 12/1976 | | UA | 66796 | 6/2004 |
| GB | 1 489 672 | 10/1977 | | WO | 82/01821 | 6/1982 |
| GB | 2 004 746 | 4/1979 | | WO | WO-86/05389 | 9/1986 |
| GB | 1 561 423 | 2/1980 | | WO | 88/01502 | 3/1988 |
| GB | 2114580 | 8/1983 | | WO | WO-88/01863 | 3/1988 |
| GB | 2 153 686 | 8/1985 | | WO | 88/08316 | 11/1988 |
| GB | 2 172 298 | 9/1986 | | WO | WO-89/06537 | 7/1989 |
| GB | 2 206 099 | 12/1988 | | WO | WO-90/05774 | 5/1990 |
| GB | 2166651 | 5/1996 | | WO | WO-91/11991 | 8/1991 |
| GB | 2337461 | 11/1999 | | WO | WO-92/00077 | 1/1992 |
| GB | 2 367 809 | 4/2002 | | WO | 92/05142 | 4/1992 |
| GB | 2 406 330 | 3/2005 | | WO | 92/05763 | 4/1992 |
| GB | 2 406 791 | 4/2005 | | WO | WO-92/11839 | 7/1992 |
| IL | 49491 | 9/1979 | | WO | 93/25189 | 12/1993 |
| IL | 0152486 | 5/2003 | | WO | 94/06440 | 3/1994 |
| JP | 60001113 | 4/1978 | | WO | WO-96/03115 | 2/1996 |
| JP | 55069682 | 5/1980 | | WO | WO-96/19921 | 7/1996 |
| JP | 57044429 | 3/1982 | | WO | 96/24325 | 8/1996 |
| JP | 56039815 | 4/1984 | | WO | 96/26711 | 9/1996 |
| JP | 61275395 | 12/1986 | | WO | WO-96/27376 | 9/1996 |
| JP | 62241701 | 10/1987 | | WO | WO-96/39119 | 12/1996 |
| JP | 6357511 | 3/1988 | | WO | 97/03638 | 2/1997 |
| JP | 63119420 | 5/1988 | | WO | WO-97/39745 | 10/1997 |
| JP | 01100111 | 4/1989 | | WO | 98/17282 | 4/1998 |
| JP | 01156906 | 6/1989 | | WO | WO-98/18472 | 5/1998 |
| JP | 2184614 | 7/1990 | | WO | WO-98/19654 | 5/1998 |
| JP | 2255890 | 10/1990 | | WO | WO-98/21955 | 5/1998 |
| JP | 04282311 | 10/1992 | | WO | WO-98/23291 | 6/1998 |
| JP | 4312521 | 11/1992 | | WO | WO-98/36733 | 8/1998 |
| JP | 5070340 | 3/1993 | | WO | 98/52536 | 11/1998 |
| JP | 5213734 | 8/1993 | | WO | WO-99/08649 | 2/1999 |
| JP | 6100414 | 4/1994 | | WO | WO-99/20250 | 4/1999 |
| JP | H06-263630 | 6/1994 | | WO | WO-99/37282 | 7/1999 |
| JP | 6329532 | 11/1994 | | WO | 99/53923 | 10/1999 |
| JP | 2007/155667 | 6/1995 | | WO | WO-00/09082 | 2/2000 |
| JP | 7215835 | 8/1995 | | WO | WO-00/15193 | 3/2000 |
| JP | 8501529 | 2/1996 | | WO | 00/23051 | 4/2000 |
| JP | 2008040899 | 2/1996 | | WO | 00/33825 | 6/2000 |
| JP | 8119831 | 5/1996 | | WO | 00/38731 | 7/2000 |
| JP | 8165218 | 6/1996 | | WO | WO-00/61076 | 10/2000 |
| JP | 8277209 | 10/1996 | | WO | WO-00/76461 | 12/2000 |
| JP | 09 084855 | 3/1997 | | WO | 01/05366 | 1/2001 |
| JP | 9099553 | 4/1997 | | WO | 01/10961 | 2/2001 |
| JP | 9110636 | 4/1997 | | WO | WO-01/08681 | 2/2001 |
| JP | 10114619 | 5/1998 | | WO | 01/53198 | 7/2001 |
| JP | 3050289 | 9/1998 | | WO | 01/54212 | 7/2001 |
| JP | 2010/332456 | 12/1998 | | WO | 01/62209 | 8/2001 |
| JP | 11501045 | 1/1999 | | WO | WO-01/54679 | 8/2001 |
| JP | 11250543 | 9/1999 | | WO | WO-01/70242 A2 | 9/2001 |
| JP | 2000/017174 | 1/2000 | | WO | 01/82890 | 11/2001 |
| JP | 2000080017 | 3/2000 | | WO | 01/85102 | 11/2001 |
| JP | 2000128734 | 5/2000 | | WO | 01/85128 | 11/2001 |
| JP | 2000191429 | 7/2000 | | WO | WO-01/82880 | 11/2001 |
| JP | 2000/239140 | 9/2000 | | WO | 01/95728 | 12/2001 |
| JP | 2000/354623 | 12/2000 | | WO | WO-02/00820 | 1/2002 |
| JP | 2000351726 | 12/2000 | | WO | 02/15860 | 2/2002 |
| JP | 2001/002526 | 1/2001 | | WO | 02/15873 | 2/2002 |
| JP | 2001019606 | 1/2001 | | WO | WO-02/28435 | 4/2002 |

| | | |
|---|---|---|
| WO | WO-02/41847 A1 | 5/2002 |
| WO | WO-02/43490 | 6/2002 |
| WO | WO-02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | WO-03/051294 | 6/2003 |
| WO | 03/055454 | 7/2003 |
| WO | WO-03/053292 | 7/2003 |
| WO | WO-03/055445 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | 2004/017962 | 3/2004 |
| WO | 2004/037197 | 5/2004 |
| WO | WO-2004/037225 | 5/2004 |
| WO | 2004/003284 | 8/2004 |
| WO | 2004/064769 | 8/2004 |
| WO | WO-2004/064833 | 8/2004 |
| WO | WO-2004/071479 A1 | 8/2004 |
| WO | 2004/078158 | 9/2004 |
| WO | WO-2004/078696 | 9/2004 |
| WO | 2004/093895 | 11/2004 |
| WO | WO-2004/112780 | 12/2004 |
| WO | WO-2005/011567 A2 | 2/2005 |
| WO | WO-2005/018530 | 3/2005 |
| WO | WO-2005/032522 | 4/2005 |
| WO | WO-2005/044219 | 5/2005 |
| WO | 2005/063224 | 7/2005 |
| WO | WO-2005/065652 | 7/2005 |
| WO | WO-2005/076697 | 8/2005 |
| WO | WO-2005/097068 A1 | 10/2005 |
| WO | 2005/102282 | 11/2005 |
| WO | WO-2005/102539 A | 11/2005 |
| WO | WO-2005/117613 | 12/2005 |
| WO | WO-2006/003461 A2 | 1/2006 |
| WO | 2006/011046 | 2/2006 |
| WO | 2006/020682 | 2/2006 |
| WO | WO-2006/010589 | 2/2006 |
| WO | 2006/028339 | 3/2006 |
| WO | WO-2006/031271 | 3/2006 |
| WO | 2006/045170 | 5/2006 |
| WO | 2006/079632 | 8/2006 |
| WO | 2006/081327 | 8/2006 |
| WO | WO-2006/091229 | 8/2006 |
| WO | WO-2006/100485 | 9/2006 |
| WO | 2006/121610 | 11/2006 |
| WO | 2006/122158 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO-2007/012977 | 2/2007 |
| WO | WO-2007/023396 | 3/2007 |
| WO | WO-2007/031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007/085902 | 8/2007 |
| WO | WO-2007/099396 | 9/2007 |
| WO | 2007/111962 | 10/2007 |
| WO | 2008/010963 | 1/2008 |
| WO | WO-2008/008397 | 1/2008 |
| WO | 2008/041045 | 4/2008 |
| WO | WO-2008/038147 | 4/2008 |
| WO | WO-2008/075207 | 6/2008 |
| WO | 2008/087148 | 7/2008 |
| WO | WO-2008/087146 | 7/2008 |
| WO | WO-2008/110872 A2 | 9/2008 |
| WO | 2008/152444 | 12/2008 |
| WO | WO-2009/007785 A2 | 1/2009 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 A2 | 7/2009 |
| WO | WO-2009/090558 A2 | 7/2009 |
| WO | WO-2009/098595 A2 | 8/2009 |
| WO | 2011/039637 | 4/2011 |
| WO | 2011/039638 | 4/2011 |

OTHER PUBLICATIONS

Barry, B.W. et al, Comparartive bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bucks, Daniel A.W., et al., "Bioavailability of Topicallly Administered Steroids; A 'Mass Balance' Technique," Journal of Investigative Dermatology, vol. 91, No. 1, Jul. 1988, pp. 29-33.

Carbowax 1000MSDS; http://www.sciencelab.com/xMSDS-Polyethylene_glycol_1000-9926622. Accessed Dec. 13, 2006, 6 pages.

Cheshire, et al., Disorders of Sweating, www.medscape.com, Semin Neurol 23(4);399-406, 2003.

Coetzee, "Acceptability and Feasibility of Micralax applicators and of methyl cellulose gel placebo for large-scale clinical trials of vaginal microbicides," Nisol.AIDS 2001. vol. 15. No. 14, pp. 1837-1842.

D.W.A. Sharp Dictionary of Chemistry, Penquin Books, 1983, 3 pages.

Dalby, "Determination of Drug Solubility in Aerosol Propellants," Pharmaceutical Research, vol. 8, No. 9, 1991, pp. 1206-1209.

Denatonium Benzoate http://www.newdruginfo.com/pharmaceopeia/usp28/v28230/usp28nf23s0_m22790.htm Accessed Dec. 9, 2008, 2 pages.

Emulsifiers with HLB values, http://www.theherbarie.com/files/resources-center/formulating/Emulsifiers_HLB_Values.pdf accessed Aug. 5, 2009 (3 pps).

Ethanol, Accessed http://www.sigmaaldrich.com/catalog.ProductDetail.do?N4=E702SIAL&N5=SEARCH_CONCAT_PNOBRAND_KEY&F=SPEC Dec. 9, 2008, 2 pages.

European Patent Application No. 06831721, Official Action, Feb. 3, 2009, 9 pages.

Flick, Cosmetic and Toiletry Formulations, vol. 5, 2nd Edition, Copyright 1996.

Fontana, Anthony, J., "Water Activity: Why It Is Important for Food Safety," International Conference on Food Safety, Nov. 16-18, 1998, 9 pages.

Galligan, John et al., "Adhesive Polyurethane Liners for Anterior Restoration," J. Dent. Res., Jul.-Aug. 1968, pp. 629-632.

Gill, A.M. et al., "Adverse Drug Reactions in a Paediatric Intensitve Care Unit," Acta Paediatr 84:438-441, 1995.

Glaser, et al., Hyperhidrosis: A Comprehensive and Practical Approach to Patient Management, Expert Rev. Dermatol, 1(6), 773-335 (2006).

Gschnait, F., et al., "Topical Indomethacin Protects from UVB and UVA Irriadiation," Arch. Dermatol. Res. 276:131-132, 1984.

Hall, Karia, "Diaper Area Hemanglomas: A Unique Set of Concerns," http://members.tripod.com/—Michelle_G/diaper.html, Dec. 1, 2006, 8 pages.

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol. Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

International Search Report and Written Opinion, International Application No. PCT/IB2006/003628, Foamix Ltd., Dec. 7, 2007, 15 pages.

International Search Report and Written Opinion, International Application No. PCT/US2007/004459, Foamix Ltd., Dec. 9, 2008, 2 pages.

International Search Report for International Application No. PCT/IB2006/003974, Feb. 25, 2008 (7 pages).

International Search Report, International Patent Application No. PCT/IB2007/003463, Foamix, Ltd., Jul. 18, 2008, 6 pages.

International Search Report, International Patent Application No. PCT/IB2007/003759, Foamix Ltd., Jul. 8, 2008 (7 pages).

Kalkan, et al., The Measurement of Sweat Intensity Using a New Technique, Tr. J. of Medical Sciences 28, 515-517 (1998).

Kathon™ CG (product information sheet by Rohm and Haas, Jun. 2006).

Kinnunen, Contact Dermatitis Sep. 1989; 21(3): 154-6, 2 pages.

Koerber, S., "Humectants and Water Activity," Water Activity News, 2000, ISSN No. 1083-3943, 8 pages.

Licking Vaginal Dryness without a Prescription. Accessed http://www.estronaut.com/a/vag_dryness.htm on Dec. 14, 2008.

Martindale, The extra pharmacopoeia [28th] edition, Eds.: Reynolds, J.E.F. and Prasad, A.B., The Pharmaceutical Press, London, pp. 862-864, 1982.

Material Safety Data Sheet, Progesterone, Apr. 26, 2006, 5 pages.

Material Safety Data Sheet, Science Lab.com, Polyethylene Glycol 1000, MSDS, Nov. 6, 2008, 6 pages.

Merriam-Webster Online Dictionaary, 2008, "Mousse," Merriam-Webster Online, Dec. 8, 2008 http://www.merriam-webster.com/dictionary/mousse, 2 pages.

Metronidazole, www.usp.org/pdf/EN/veterinary/metronidazole.pdf. accessed Sep. 10, 2009, 4 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1996, pp. 1213-1218.

OM Cinnamate. http://www.makingcosmetics.com/sunscreens/OM-Cinnamate-p102.html accessed Sep. 26, 2009, 1 page.

Pendergrass, "The shape and dimensions of the human vagina as seen in three-dimensional vinyl polysiloxane casts," Gynecol. Obstet. Invest. 1996:42(3):178-82 (abstract).

Progesterone MSDS. http://www.usp.org.pdf.EN/referenceStandards/msds/1568007.pdf on Dec. 14, 2002, 5 pages.

Savin, et al., "Tinea versicolor treated with terbinafine 1% solution," Int J. Dermatol. Nov. 1999; 38(11), pp. 863-865.

Schmidt A., "Malassezia furfur: a fungus belonging to the physiological skin flora and its relevance in skin disorders," Curtis., Jan. 1997: 59(1), pp. 21-24 (abstract).

Scott as Published in Pharmaceutical Dosage Forms; Disperse Systems, vol. 3, Copyright 1998.

Shear, et al., "Pharmacoeconomic analysis of topical treatments for linea infections," Pharmacoeconomics. Mar. 1995; 7(3); pp. 251-267 (abstract only).

Sigma Aldrich, "HLB-Numbers in Lithography Nanopatterning," http://www.signaaldrich.com/materials-science/micro-and-nanoelectronics/lithography-nanopatterning/hib-numbers.html, accessed: Feb. 2, 2009, pp. 1-3.

Sigma-Aldrich, Material Safety Data Sheet, Hydroxyethyl Cellulose, Mar. 3, 2004, 5 pages.

Skin Biology, CP Serum—Copper-Peptide Serum for Skin Regeneration and Reducing Wrinkles, Skin Biology, http://web.archive.org/web/20030810230608/http://www.skinbio.com/opserum.html. Dec. 1, 2006, 21 pages.

Squire. J, "A randomised, single-blind, single-centre clinical trial to evaluate comparative clinical efficacy of shampoos containing ciclopirox olamine (1.5%) and salicyclic acid (3%), or ketoconazole (2%, Nizoral) for the treatment of dandruff/seborrhoeic dermatitis," Dermatolog Treat. Jun. 2002;13(2):51-60 (abstract only).

Tan et al., "Effect of Carbopol and Polyvinylpyrrolidone on the Mechanical, Rheological, and Release Properties of Bioadhesive Polyethylene Glycol Gels," AAPS PharmSciTech. 2000; 1(3) article 24 (2000), 10 pages.

Torres-Rodriguez, JM., "New topical antifungal drugs," Arch Med Res. 1993 Winter; 24(4), pp. 371-375 (abstract).

Toxicology and Carcinogenesis Studies of t-Butyl Alcohol (CAS No. 75-65-0) in F344/N Rats and B6C3F1, Mice (Drinking Water Studies), http://ntp.niehs.nih.gob/?objectid-=0709F73D-A849-80CA-5P8784E866B576D1.Accessed Dec. 9, 2008.

Wormser et al., Early and topical treatment with povidone-iodine ointment reduces, and sometimes prevents, skin damage following heat stimulus. Letters to the Editor, Burns, 1998, 24, 383.

Wormser et al., Protective effect of povidone-iodine ointment against skin lesions induced by sulphur and nitrogen mustards and by non-mustard vesicants. Arch. Toxicol., 1997, 71, 165-170.

Edirisinghe, et al., "Effect of fatty acids on endothellum-dependent relaxation in the rabbit aorta", Clin Sci (Lond). Aug. 2006; 111(2): 145-51.

Encyclopedia of Pharmaceutical Technology, Second Edition, vol. 3, Copyright 2002.

Leung, et al., "Bioadhesive Drug Delivery in Water-Soluble Polymers," American Chemical Society, Chapter 23, 1991, pp. 350-366.

http://web.archive.org/web/20000106225413/http://pharmacy.wilkes.edu/kibbeweb/lab7.html, Characteristics of Surfactants and Emulsions, Jan. 29, 2010, 5 pages.

Kanamoto, et al., "Pharmacokinetics of two rectal dosage forms of ketoprofen in patients after anal surgery," J Pharmacobiodyn., Mar. 1968; 11(3):141-5.

http://www.agworkshop.com/p3.asp, AG&Co. Essential oil workshop.

Hakan, et al., "The protective effect of fish oil enema in acetic acid and ethanol induced colitis," The Turkish Journal of Gasroenterology, 2000, vol. 11, No. 2, pp. 151-161.

MMP Inc. International Development and Manufacturing, "Formulating specialities," http://mmpinc.com.

Tarumoto, et al., Studies on toxicity of hydrocortisone 17-butyrate 21-propionate-1. Acute toxicity of hydrocortisone 17-butyrate 21-propionate and its analogues in mice, rats and dogs (author's trans), J Toxicol Sci., Jul. 1981; 6 Suppl: 1-16.

http://ibabydoc.com/online/diseaseeczema.asp., Atopic Dermatitis, Copyright 2000.

Machine Translation of JP-08165218 (1996).

U.S. Appl. No. 60/789,186, filed Apr. 4, 2006, Tamarkin.
U.S. Appl. No. 60/815,948, filed Jun, 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.

hydroxyethylcellulose. Http://terpconnect.umd.edu/-choi/MSDS/Sigma-Aldrich/HYDROXYETHYL%20CELLULOSE, 5 pages, Jan. 14, 2004.

Molan, Peter Clark, "World Wide Wounds," Dec. 2001, 13 pages.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Skin Biology, CP Serum—Copper-Peptide Scrum for Skin Regeneration and Reducing Wrinkles, Skin Biology, http;//web.archive.org/web/20030810230608/http://www.skinbio.com/cpserum.- html, Dec. 1, 2008, 21 pages.

Third Party Submission for U.S. Appl. No. 12/014,088, filed Feb 4, 2009, 4 pages.

"Burn patients need vitamin D supplements." *Decision News Media*, Jan. 23, 2004, http://www.nutraingredients.com/Research/Burn-patients-need-vitamin-D-supplements, Accessed: May 5, 2010.

"HLB Systems", http://pharmcal.tripod.com/ch17.htm, Accessed Sep. 17, 2010, pp. 1-3.

"Minocycline" accessed on Oct. 21, 2011 at en.wikipedia.org/wiki/Minocycline, 7 pages.

"Reaction Rate" Accessed at en.wikipedia.org/wiki/Reaction_rate on Dec. 18, 2011, 6 pages.

'Niram Chemicals' [online]. Niram Chemicals, [retrieved on Jul. 17, 2012]. Retrieved from the Internet: <URL: http://www.indiamart.com/niramchemicals/chemicals.html>, 7 pages.

'Surfactant' [online]. Wikipedia, 2010, [retrieved on Oct. 24, 2010]. Retrieved from the Internet: <URL: http://en.wikipedia.org/wiki/Surfactant>, 7 pages.

Adachi, Shuji. "Storage and Oxidative Stability of O/W/ Nano-emulsions." Foods Food Ingredients. J. Jpn. vol. 209, No. 11. 2004. 1 page.

Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Chevrant-Breton, et al., "Etude du Traitement Capillaire <<Bioscalin>> dans les Alopecics Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Colloidal Silica. Retrieved online on Jun. 4, 2011. <URL:http://www.grace.com/engineeredmaterials/materialsciences/colloidalsilica/defaultaspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

Dawber, et al., "Hypertrichosis in Females Applying Minoxidil Topical Solution and in Normal Controls", JEADV, 17:271-275 (2003).

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edwards, "Imiquimod in Clinical Practice", J. Am Acad Dermatol., 43(1, Pt 2):S12-S17 (2000)—Abstract, 1 page.

Esposito, E. et al. "Nanosystems for Skin Hydration: A Comparative Study." International Journal of Cosmetic Science. 29. 2007. pp. 39-47.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Gallarate, et al., "On the Stability of Ascorbic Acid in Emulsified Systems for Topical and Cosmetic Use", International Journal of Pharmaceutics, 188:233-241 (1999).

Gelbard et al. "Primary Pediatric Hyperhidrosis: A Review of Current Treatment Options." Pediatric Dermatology. 2008. 25 (6). pp. 591-598.

Gladkikh, "Ascorbic Acid and Methods of Increasing its Stability in Drugs", Translated from Khimiko-Farmatsevticheskii Zhurnal, 4(12):37-42 (1970)—1 page.

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Hallstar. Retrieved online on Jun. 4, 2011. <URL:http://www.hallstar.com/pis.php?product=1H022>. 1 page.

Hargreaves, "Chemical Formulation, An Overview of Surfactant-Based Preparations Used in Everyday Life", *The Royal Society of Chemistry*, pp. 114-115 (2003).

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Heart Failure, The Merck Manual, 2008 <<http://www.merck.com/mmhe/sec03/ch025/ch025a.html>> 12 pages.

Hormones. Http://www.greenwillowtree.com/Page.bok?file=libido.html. Jan. 2001.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theal17c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kang, et al., "Enhancement of the Stability and Skin Penetration of Vitamin C by Polyphenol", Immune Nctw., 4(4):250-254 (2004)—Abstract, 1 page.
Karasu, T.B. et al., "Treatment of Patients with Major Depressive Disorder, Second Edition," pp. 1-78, 2000.
Kim, "Stability of Minoxidil in Aqueous Solution", Yakhak Hoechi, 30(5):228-231 (1986)—Abstract, 1 page.
Kleber, M.D., H.D. et al., "Treatment of Patients with Substance Use Disorders, Second Edition," pp. 1-276, 2006.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5): 269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Li, et al., "Solubility Behavior of Imiquimod in Alkanoic Acids", Abstract 3029, Pharmaceutical Research, vol. 14, No. 11 Supplemental (Nov.), p. S475 (1997), 2 pages.
Lippacher, A. et al. "Liquid and Semisolid SLN Dispersions for Topical Application Rheological Characterization." European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale. 33 ed. London, Bath Press, 2002. pp. 1073 and 1473.
Merck index, 10th edition, Merck & Co., Inc.: Rahway, NJ 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. 13$^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Messenger, et al., "Minoxidil: Mechanisms of Action on Hair Growth", British Journal of Dermatology, 150:186-194 (2004).
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
Neutrogena. Http://www.cosmetoscope.com/2010/04/neutrogeaclinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.

No Author Listed. "Opitmization of Nano-Emulsions Production by Microfluidization." European Food Research and Technology. vol. 225, No. 5-6. Sep. 2007. Abstract. 1 page.
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural 503-507 and synthetic triphylite," *J. of Power Sources*, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen ÒTR-2NF)," International Journal of Cosmetic Science, vol. 2(2): abstract only. Dec. 24, 2001, 1 page.
Skin Deep Cosmetics. PPG-40-PEG-60 Lanolin Oil http://www.cosmeticsdatabase.com/ingredient/722972/PPG-40-PEG-60 Lanolin Oil/?ingred06=722972. 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle et al., Uptake of minoxidil from a new foam formulation devoid of propylene glycol to hamster ear hair follicles, J. Invest. Dermatol., 2005, 124(4), A101.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Surfactant. Chemistry Glossary. Http://chemistry.about.com/od/chemistryglossary/g/surfactant.htm, 2012, 1 page.

Sweetman, Sean C. Martindale: The Complete Drug Reference. 33rd Edition. London. Pharmaceutical Press. Jun. 21, 2002. pp. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tanhehco, "Potassium Channel Modulators as Anti-Inflammatory Agents", Expert Opinion on Therapeutic Patents, 11(7):1137-1145 (2001)—Abstract, 3 pages.

Tata, et al., "Penetration of Minoxidil from Ethanol Propylene Glycol Solutions: Effect of Application Volume On Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Yamada and Chung, "Crystal Chemistry of the Olivine-Type $Li(Mn_yFe_{1-y})PO_4$ and $(Mn_yFe_{1-y})PO_4$ as Possible 4 V Cathode Materials for Lithium Batteries," J. Electrochemical Soc., 2001, 148(8): A960-967.

"Coal tars and coal-tar pitches," Report on Carcinogens, Twelfth Edition, 2011, 3 pages.

Adisen et al. "Topical tetracycline in the treatment of acne vulgaris," J Drugs Dermatol., 2008, 7:953-5.

Baskaran et al., "Poloxamer-188 improves capillary blood flow and tissue viability in a cutaneous burn wound," J. Surg. Res., 2001, 101(1):56-61.

Bell-Syer et al. "A systematic review of oral treatments for fungal infections of the skin of the feet," J. Dermatolog. Treat., 2001, 12:69-74.

Boehm et al. 1994, "Synthesis of high specific activity [.sup.3 H]-9-cis-retinoic acid and its application for identifying retinoids with unusual binding properties," J. Med. Chem., 37:408-414.

Carapeti et al., "Topical diltiazem and bethanechol decrease anal sphincter pressure and heal anal fissures without side effects," Dis Colon Rectum, 2000, 43(10):1359-62.

Cook and Mortensen, "Nifedipine for treatment of anal fissures," Dis Colon Rectum, 2000, 43(3):430-1.

Dumortier et al., "A review of poloxamer 407 pharmaceutical and pharmacological characteristics," Pharmaceutical Res., 2006, 23(12):2709-2728.

Ebadi et al., "Healing effect of topical nifedipine on skin wounds of diabetic rats," DARU, 2003, 11(1):19-22.

Effendy and Maibach. "Surfactants and Experimental Irritant Contact Dermatitis." Contact Dermatol., 1995, 33:217-225.

Elias and Ghadially, "The aged epidermal permeability barrier," Clinical Geriatric Medicine, Feb. 2002, pp. 103-120.

Fantin et al., "Critical influence of resistance to streptogramin B-type antibiotics on activity of RP 59500 (Quinupristin-dalfopristin) in experimental endocarditis due to Staphylococcus aureus," Antimicrob Agents and Chemothery, 1999, 39:400-405.

Fluhr et al., "Glycerol accelerates recovery of barrier function in vivo," Acta Derm. Venereol,. 1999, 79:418-21.

Garti et al. "Sucrose Esters microemulsions," J. Molec. Liquids, 1999, 80:253-296.

Hammer et al. "Anti-Microbial Activity of Essential Oils and other Plant extracts," J. Applied Microbiology, 1999, 86:985-990.

Hwang et al. "Isolation and identification of mosquito repellents in Artemisia vulgaris," J. Chem. Ecol., 11: 1297-1306, 1985.

Knight et al., "Topical diltiazem ointment in the treatment of chronic anal fissure," Br. J. Surg., 2001, 88(4):553-6.

Kucharekova et al., "Effect of a lipid-rich emollient containing ceramide 3 in experimentally induced skin barrier dysfunction," Contact Dermatitis, Jun. 2002, pp. 331-338.

Leive et al, "Tetracyclines of various hydrophobicities as a probe for permeability of Escherichia coli outer membrane," Antimicrobial Agents and Chemotherapy, 1984, 25:539-544.

Luepke and Kemper, "The HET-CAM Test: An Alternative to the Draize Eye Test," FD Chem. Toxic., 1986, 24:495-196.

Osborne and Henke, "Skin Penetration Enhancers Cited in the Technical Literature," Pharm. Technology, Nov. 1997, pp. 58-86.

Padi. "Minocycline prevents the development of neuropathic pain, but not acute pain: possible anti-inflammatory and antioxidant mechanisms," Eur J. Pharmacol, 2008, 601:79-87.

Palamaras and Kyriakis, "Calcium antagonists in dermatology: a review of the evidence and research-based studies," Derm. Online Journal, 2005, 11(2):8.

Passi et al., Lipophilic antioxidants in human sebum and aging, Free Radical Research, 2002, pp. 471-477.

Perrotti et al., "Topical Nifedipine With Lidocaine Ointment vs. Active Control for Treatment of Chronic Anal Fissure," Dis Colon Rectum, 2002, 45(11):1468-1475.

Repa et al. "All-trans-retinol is a ligand for the retinoic acid receptors," Proc. Natl. Acad Sci, USA, 90: 7293-7297, 1993.

Ruledge, "Some corrections to the record on insect repellents and attractants," J. Am. Mosquito Control Assoc, 1988, 4(4): 414-425.

Sakai et al., "Characterization of the physical properties of the stratum corneum by a new tactile sensor," Skin Research and Technology, Aug. 2000, pp. 128-134.

Schaefer, "Silicone Surfactants," Tenside, Surfactants. Deterg., 1990, 27(3): 154-158.

Simoni et al., "Retinoic acid and analogs as potent inducers of differentiation and apoptosis. New promising chemopreventive and chemotherapeutic agents in oncology," Pure Appl Chem., 2001, 73(9):1437-1444.

Smith, "Hydroxy acids and skin again," Soap Cosmetics Chemical Specialties, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," European J. Pharm. Biopharm., 1998, 46(3):265-71.

Todd et al. "Volatile Silicone Fluids for Cosmetics," 91 Cosmetics and Toiletries, 1976, 27-32.

USP23/NF 18 The United States Pharmacopeia: The National Formulary, US Pharmacopoeia, 1995, p. 10-14.

Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.

Van Slyke, "On the measurement of buffer values and on the relationship of buffer value to the dissociation constant of the buffer and the concentration and reaction of the buffer solution," *J. Biol. Chem.*, 1922, 52:525.

Van Cutsem et al., "The antiinflammatory efects of ketoconazole," *J. Am. Acad. Dermatol.*,1991, (2 pt 1):257-61.

Wang and Chen, "Preparation and surface active properties of biodegrabable dextrin derivative surfactants," *Colloids and Surfaces A: Physicochemical and Engineering Aspects*, 2006, 281(1-3):190-193.

Weindl et al., "Hyaluronic acid in the treatment and prevention of skin diseases: molecular biological, pharmaceutical and clinical aspects," *Skin Pharmacology and Physiology*, 2004, pp. 207-213.

Xynos et al., "Effect of nffedipine on rectoanal motility," *Dis Colon Rectum*, 1996, 39(2):212-6.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with $Cu^{2+}$ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

Official action from European Application No. 06809259.2, dated Jan. 29, 2009, 6 pages.

Official action from European Application No. 06809259.2, dated Mar. 18, 2010, 5 pages.

Official action from European Application No. 06809259.2, dated Sep. 23, 2011, 6 pages.

http://www.agworkshop.com/p3.asp, AG&Co. Essential oil workshop. 1 page. Accessed Jan. 31, 2010.

MMP Inc. International Development and Manufacturing, "Formulating specialities," http://mmpine.com, 3 pages. Feb. 2, 2010.

Candida albicans

Composition A effective

Compositions B and C ineffective

Trichophyton rubrum

Compositions A, B and C effective

Trichophyton mentagrophytes

Compositions A and B effective

Composition C ineffective

Microsporum canis

Composition A and B effective

Composition C ineffective

FOAMABLE VEHICLE AND PHARMACEUTICAL COMPOSITIONS THEREOF

CROSS REFERENCE TO RELATED APPLICATIONS

This application is a continuation of and claims the benefit of priority under 35 U.S.C §120 to U.S. patent application Ser. No. 11/430,599, filed on May 9, 2006, entitled "Foamable Vehicle and Pharmaceutical Compositions Thereof," which claims the benefit under 35 U.S.C. §119(e) of U.S. Provisional Patent Application No. 60/679,020, filed on May 9, 2005, entitled "Hygroscopic Anti-Infective Compositions" and of U.S. Provisional Patent Application No. 60/784,793, filed on Mar. 21, 2006, entitled "Polyol Foamable Vehicle and Pharmaceutical Compositions Thereof," and which is a continuation-in-part application of co-pending U.S. patent application Ser. No. 10/835,505, filed on Apr. 28, 2004, which claims the benefit of priority under 35 U.S.C. §119(e) to U.S. Patent Application Ser. No. 60/530,015, filed on Dec. 16, 2003, and U.S. Patent Application Ser. No. 60/492,385, filed on Aug. 4, 2003, all entitled "Oleaginous Pharmaceutical Foam" and all of which are hereby incorporated in their entirety by reference.

BACKGROUND OF THE INVENTION

This invention relates to foamable pharmaceutical and cosmetic compositions.

External topical administration is an important route for the administration of drugs in disease treatment. Many groups of drugs, including, for example, antibiotic, anti-fungal, anti-inflammatory, anesthetic, analgesic, anti-allergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds.

Foams and, in particular, foams that are substantially based on non-aqueous solvents are complicated systems which do not form under all circumstances. US Pat. Appl. No. 20050031547 relates to stable oleaginous cosmetic or therapeutic foam compositions containing certain active agents, having unique therapeutic properties and methods of treatment using such compositions. The foamable carrier includes at least one solvent selected from a hydrophobic solvent, a silicone oil, an emollient, a co-solvent, and mixtures thereof, wherein the solvent is present at a concentration of about 70% to about 96.5% by weight of the total composition, at least a non-ionic surface-active agent at a concentration of about 0.1% to less than about 10% by weight of the total composition; at least one gelling agent at a concentration of about 0.1% to about 5% by weight of the total composition; a therapeutically effective amount of at least one active agent; and at least one liquefied or compressed gas propellant, at a concentration of about 3% to about 25% by weight of the total composition.

WO 00/09082 teaches an anhydrous cleansing composition for topical application to human skin, comprising an ionic surfactant, glycerine, propylene glycol and water insoluble benefit agents. According to the examples of WO 00/09082, the concentration of the ionic surfactant is in the range of 18-22%.

U.S. Pat. No. 6,765,001 comprises a composition, method of enhancing potency and method of delivering corticosteroids in a vehicle comprising two or more penetration enhancers selected from the group consisting of diisopropyl adipate, dimethyl isosorbide, propylene glycol, 1,2,6-hexapetriol, and benzyl alcohol; and one or more of the group consisting of solvents and emulsifiers.

WO91/11991 teaches an essentially non-aqueous and non-oily foamable composition, that can be used for rectal administration of pharmaceuticals, comprising a liquid polar polyol or polyol mixture, a pharmaceutically active ingredient and at least one foam stabilizing and emulsifying surfactant. However, this foam composition is associated with disadvantages and the purposes of the present invention are not attained (see comparative example below).

There remains an unmet need for improved, easy to use, stable and non-irritating anti-infective foam formulations, intended for treatment of dermal and mucosal tissues. Particularly, there remains an unmet need for improved, easy to use, stable and non-irritating anti-infective foam formulations, with unique therapeutic properties.

SUMMARY OF THE INVENTION

In one aspect, the invention provides a hygroscopic pharmaceutical composition including at least one hygroscopic substance at a sufficient concentration to provide an Aw value of the hygroscopic pharmaceutical composition of less than 0.9 and an anti-infective agent; or the Aw value is in the range of about 0.8 and about 0.9; (2) about 0.7 and about 0.8; and (3) less than about 0.7

In one or more embodiments, the hygroscopic pharmaceutical composition further includes at least one component, selected from the group consisting of about 0.01% to about 5% by weight of at least one polymeric agent selected from a bioadhesive agent, a gelling agent, a film forming agent and a phase change agent; and about 0.2% to about 5% by weight of a surface-active agent.

In one or more embodiments, the hygroscopic substance is selected from the group consisting of polyethylene glycols (PEGs), surfactants comprising PEG, polyols, monosaccharides, disaccharides, oligosaccharides and sugar alcohols in an amount to provide hygroscopic properties, and honey.

In another aspect, the invention provides a foamble pharmaceutical carrier including about 50% to about 98% of a polar solvent selected from the group consisting of (1) a polyol and (2) a polyethylene glycol (PEG); 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

In one or more embodiments, the compositions further comprise up to 10% of water.

In one or more embodiments, the composition is substantially non-aqueous and/or substantially alcohol-free.

In one or more embodiments, the composition further comprises a therapeutically effective concentration of one or more active agents.

In one or more embodiments, the polyol is selected from the group consisting of a diol, a triol and a saccharide, and the triol may be selected from the group consisting of glycerin, butane-1,2,3-triol, butane-1,2,4-triol and hexane-1,2,6-triol, or the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol.

In one or more embodiments, the polyol consists of at least one diol and at least one triol, and wherein the ratio between the diol and triol is between 9:1 and 1:1.

In one or more embodiments, the composition includes a mixture of at least one polyol and at least one PEG, and the PEG may be selected from the group consisting of PEG 200, PEG 300, PEG 400, PEG 600, PEG 1000, PEG 4000, PEG 6000 and PEG 8000, or the composition contains one or more PEGs in a concentration to provide viscosity of less than 12,000 CPs.

In one or more embodiments, the composition includes a secondary polar solvent selected from the group consisting of dimethyl isosorbide, tetrahydrofurfuryl alcohol polyethyleneglycol, ether, DMSO, a pyrrolidone, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid, or the secondary polar solvent is dimethyl isosorbide.

In one or more embodiments, the composition includes (1) at least one polar solvent selected from a diol, a triol and PEG, and (2) at least one secondary polar solvent, and for example, the polar solvent comprises a mixture of at least one polyol and at least one PEG, and for example, the polyol comprises a mixture of at least two polyols.

In one or more embodiments, the ratio between the polyol and/or PEG and the secondary polar solvent is between 9:1 and 1:1.

In another aspect of the inventin, a method of treating a disorder of mammalian subject includes administering a foamable therapeutic composition to a target area, the composition comprising a therapeutically effective concentration of an active agent, about 50% to about 98% of a polar solvent selected from the group consisting of (1) a polyol; and (2) a polyethylene glycol; 0% to about 48% of a secondary polar solvent; about 0.2% to about 5% by weight of a surface-active agent; about 0.01% to about 5% by weight of at least one polymeric agent; and a liquefied or compressed gas propellant at a concentration of about 3% to about 25% by weight of the total composition.

In one or more embodiments, the target site is selected from the group consisting of the skin, a body cavity, a mucosal surface, the nose, the mouth, the eye, the ear canal, the respiratory system, the vagina and the rectum.

BRIEF DESCRIPTION OF THE DRAWINGS

Various objects, features, and advantages of the present invention can be more fully appreciated with reference to the following detailed description of the invention when considered in connection with the following drawings, in which like reference numerals identify like elements. The following drawings are for the purpose of illustration only and are not intended to be limiting of the invention, the scope of which is set forth in the claims that follow.

DETAILED DESCRIPTION OF THE INVENTION

Figure 1A:
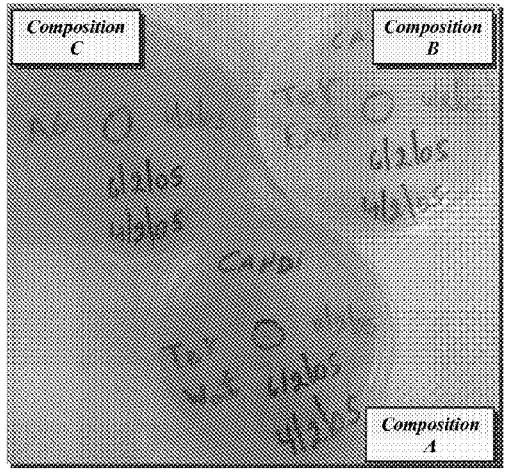
FIG. 1A-D illustrates the in vitro effect of effect of Composition A, consisting of 2% terbinafine, 95.3% gr. polyethylene glycol, 0.5% hydroxypropyl cellulose and 2.2% steareth-2, in comparison with Composition B (an oil in water emulsion containing 2% terbinafine) and Composition C a commercial 1% bifonazole cream, in the treatment of three fungal strains (*microsporum canis, trichophyton mentagrophytes* and *trichophyton rubrum*) and one yeast (*candida albicans*).

The present invention relates to a composition for use as foamable vehicle composition.

According to one or more embodiments of the present invention, the foamable carrier, includes:
 a. about 50% to about 98% of a polar solvent selected from the group consisting of (1) a polyol; and (2) a polyethylene glycol;
 b. 0% to about 48% of a secondary polar solvent;
 c. about 0.2% to about 5% by weight of a surface-active agent;
 d. about 0.01% to about 5% by weight of at least one polymeric agent; and
 e. a liquefied or compressed gas propellant at a concentration of about 3% to about 25% by weight of the total composition.

All % values are provided on a weight (w/w) basis.

Water, up to 25% of the composition, and more preferably up to 10%, and optional ingredients are added to complete the total mass to 100%. In certain cases, the composition contains two active agents that require different pH environments in order to remain stable. For example, corticosteroids are typically stable at acidic pH (they have a maximum stability at a pH of about 4-6) and vitamin D analogues are typically stable at basic pH (they have a maximum stability at pH values above about 8). In other cases, the active agent degrades in the presence of water, and therefore, in such cases the present of water in the composition is not desirable. Thus, in certain preferred embodiments, the composition is substantially non-aqueous. The term "substantially non-aqueous" is intended to indicate that the composition has a water content below about 5%, preferably below about 2%, such as below about 1.5%.

Upon release from an aerosol container, the foamable carrier forms an expanded foam suitable for the treatment of an infected surface and for topical administration to the skin, a body surface, a body cavity or a mucosal surface.

The identification of a "polar solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

Polyol

In an embodiment of the present invention, the polar solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2, 56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is (CH2O)n and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol). Mixtures of polyols, including (1) at least one polyol selected from a diol and a triol; and (2) a saccharide are contemplated within the scope of the present invention.

Polyethylene Glycol

In an embodiment of the present invention, the polar solvent consists of a polymerized ethylene glycol, namely polyethylene glycol, which is also termed "PEG". Exemplary PEGs are provided in the following table.

| Composition | Av. Molecular weight | Appearance | Melting point (° C.) |
| --- | --- | --- | --- |
| PEG 200 | 190~210 | Oily liquid | |
| PEG 300 | 285~315 | Oily liquid | |
| PEG 400 | 380~420 | Oily liquid | |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present invention, the PEG is selected from the group consisting of PEG 200, PEG 300, PEG 400, PEG 600, PEG 1000, PEG 4000, PEG 6000 and PEG 8000. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters, of less than 12,000 CPs, and more preferably, less than 10,000 CPs.

Secondary Polar Solvent

Optionally, a secondary polar solvent is added to the foamable composition of the present invention. The secondary polar solvent is selected from a variety of organic solvents that are typically miscible on both water and oil. Examples of polar solvent that can be contained in the foamable carrier of the present invention include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Solubilization and Penetration Enhancement

In many cases, polyols, PEGs and polar solvents possess a high solubilizing power and thus, they can enable increased concentrations of a pharmaceutical active agent. Polyols, PEGs and polar solvents are also known for their skin penetration enhancement properties. These properties enable high drug bioavailability in the target area of treatment, resulting in an enhanced therapeutic effect. Occasionally, combinations of a polyol, PEGs and a secondary polar solvent, exhibit an increased permeability across the skin, as suggested, for example, in Eur J Pharm Biopharm. 1998 November; 46(3):265-71.

Thus, in one or more embodiments, the foamable carrier contains (1) at least one polar solvent, selected from a polyol (selected from a diol and a triol) and PEG; and (2) at least one secondary polar solvent.

In one or more embodiments, the foamable carrier contains (1) a mixture of at least two polyols; and (2) at least one secondary polar solvent. In additional embodiments, the foamable carrier contains a mixture of at least one polyol and at least one PEG; yet in other embodiments the foamable carrier contains (1) a mixture of at least one polyol and at least one PEG and (2) at least one secondary polar solvent.

According to certain embodiments the ratio between the polyol and/or PEG and the secondary polar solvent is between 9:1 and 1:1.

In certain embodiments, the polyol is selected from the group consisting of propylene glycol, hexylene glycol and glycerin (and mixtures thereof); and the secondary polar solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Short chain alcohols, such as ethanol and propanol are known as polar solvents, however, according to one or more embodiments, the composition of the present invention is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable polar solvents due to their skin-irritating effect.

Thus, in certain embodiments, the composition is substantially alcohol-free and includes less than about 5% final concentration of lower alcohols, preferably less than about 2%, more preferably less than about 1%. However, in other embodiments, a short chain alcohol can be included in the composition, as long as the ratio between the short chain alcohol and the polyol is less than 1:4 by weight.

Polymeric Agent

The composition of the present invention contains a polymeric agent. It has been documented that the presence of a polymeric agent is necessary for the creation of foam, having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional polar solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981.

Other polymeric agents are suitable for use according to the present invention provided that they are soluble or readily dispersible in the polyol; or in the mixture of a polyol and an additional polar solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 4,000, PEG 6,000 and PEG 10,000) also have gelling capacity and while they are considered herein as "secondary polar solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface-Active Agent

The composition of the present invention further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments the composition contains a single surface active agent having an HLB value between about 7 and 12, or more than one surface active agent and the weighted average of their HLB values is between about 7 and about 12.

Preferably, the composition of the present invention contains a non-ionic surfactant. Nonlimiting examples of possible non-ionic surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene)alkylyl ethers, such as poly(oxyethylene)cetyl ether, poly(oxyethylene)palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, and mono-, di- and tri-esters of sucrose with fatty acids (sucrose esters).

Non-limiting examples of non-ionic surfactants that have HLB of about 7 to about 12 include PEG 100 stearate (HLB=11), Laureth 4 (HLB=9.7) and cetomacrogol ether (e.g., polyethylene glycol 1000 monocetyl ether).

Yet, in additional embodiments, the composition contains a single surface active agent or a combination of surface active agents having an HLB values between about 9 and about 14; and in other embodiments, the composition contains one or more surface active agents, having an HLB value between about 2 and about 9.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

Thus, in a preferred embodiment, the surface active agent, the composition contains a non-ionic surfactant, or a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In further embodiments, surface active agent comprises a combination of a non-ionic surfactant and an ionic surfactant, at a ratio of between 1:1 and 20:1. The concentration of the surface active agent is between about 0.1% and about 5%.

Hydrophobic Solvent

Optionally, the foamable carrier further contains at least one hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxanes, polyaryl siloxanes, polyalkylaryl siloxanes and polyether siloxane copolymers, polydimethylsiloxanes(dimethicones) and poly(dimethylsiloxane)-(diphenyl-siloxane)copolymers.

Foam Adjuvant

Optionally, a foam adjuvant is included in the foamable carriers of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Additional Components

In an embodiment of the present invention, a composition of the present invention includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment of the present invention, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment of the present invention, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof.

In an embodiment of the present invention, the additional component is a humectant. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

In an embodiment of the present invention, the additional component is a preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment of the present invention, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl) ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly(dimethylaminoethyl-methacryl-ate), quaternised poly(vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

Propellants

Examples of suitable propellants include volatile hydrocarbons such as butane, propane, isobutane and fluorocarbon gases, or mixtures thereof.

In certain embodiments, fluorohydrocarbon propellants, other than chloro-fluoro carbons (CMCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

The propellant makes up about 5-25 wt % of the foamable composition. Aerosol propellants are used to generate and administer the foamable composition as a foam. The total composition including propellant, foamable compositions and optional ingredients is referred to as the foamable composition.

Hygroscopic Property of the Composition

A hydroscopic substance is a substance that absorbs water readily from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Addition of a hygroscopic substance to an aqueous solution in which a microorganism is growing will have the effect of lowering the Aw, with a consequent effect upon cell growth. Every microorganism has a limiting Aw, below which it will not grow, e.g., for *streptococci, klebsiella* spp., *escherichia coli, clostridium perfringens*, and *pseudomonas* spp. the Aw value is 0.95. *Staphylococcus aureus* is most resistant and can proliferate with an Aw as low as 0.86.

The water activity of a product can be determined from the relative humidity of the air surrounding the sample when the air and the sample are at equilibrium. Measurement is performed by placing a sample in an enclosed space where this equilibrium can take place. Once this occurs, the water activity of the sample and the relative humidity of the air are equal. The measurement taken at equilibrium is called an equilibrium relative humidity or ERH. The relationship between the water activity and ERH is in accordance with the following formula:

$$Aw=ERH/100$$

Various types of water activity instruments are commercially available. One exemplary instrument uses chilled-mirror dewpoint technology while other instruments measure relative humidity with sensors that change electrical resistance or capacitance.

Polyols, PEGs and other polar solvents have a great affinity for water, and as such, they exhibit hygroscopic properties. The concentration of the polyol, the PEG and/or other polar solvents determines the Aw of the carrier. In one or more embodiments, the polyols, the PEG and/or the secondary polar solvent is contained in the composition of the present invention at a sufficient concentration to provide an Aw value of the hygroscopic carrier of less than 0.9. In other embodiments, the concentration of the polyol, the PEG and/or secondary polar solvent in the composition is selected to provide a Aw value selected from the ranges of (1) about 0.8 and about 0.9; (2) about 0.7 and about 0.8; and (3) less than about 0.7.

As such, a composition containing a polyol, a PEG with or without a secondary polar solvent can be used as topical treatment of superficial infectious conditions.

The advantage of providing a hygroscopic composition in a pressurized packaging presentation is readily perceived. The usage of all other presentations, such as solutions, creams, lotions, ointments and the like involves repeated opening of the package closure, resulting in absorption of water from the surrounding environment and a subsequent elevation of the Aw (thus lowering the hygroscopicity of the product, and therefore decreasing its anti-infective potential. By contrast, a pressurized packaging does not allow for any humidity to be absorbed by the preparation, and therefore, the hygroscopic character of the composition cannot be damaged.

In one or more embodiments, the hygroscopic composition of the present invention further contains an anti-infective agent, selected from the group of an antibiotic agent, an antibacterial agent, an antifungal agent, an agent that controls yeast, an antiviral agent and an antiparasitic agent. Combining the anti-infective effect of a hygroscopic composition, which acts through a dehydration mechanism, with an additional anti-infective agent that acts through alternate mechanisms results in a synergistic effect and consequently higher success rate of the treatment.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of at least one year, or preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The foam of the present invention has several advantages, when compared with hydroalcoholic foam compositions, such as described in WO 2004/071479:

(1) Breakability. The foam of the present invention is thermally stable. Unlike hydroalcoholic foam compositions of the prior art, the foam of the present invention is not "quick breaking", i.e., it does not readily collapse upon exposure to body temperature environment. Sheer-force breakability of the foam is clearly advantageous over thermally induced breakability, since it allows comfortable application and well directed administration to the target area.

(2) Skin drying and skin barrier function. Short chain alcohols are known to dry the skin and impair the integrity of the skin barrier. By contrast, including a film forming agent in the composition of the present invention foes not cause unwanted skin barrier damage.

(3) Irritability. Due to the lack of alcohol and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable composition of the present invention is an ideal vehicle for active pharmaceutical ingredients and active cosmetic ingredients. In the context of the present invention, active pharmaceutical ingredients and active cosmetic ingredients are collectively termed "active agent" or "active agents". A foamable composition, comprising an active agent has the following advantages:

1. The foamable composition provides a preferred solvent for active agents, particularly water-insoluble agents.
2. The inclusion of a polyol and/or a PEG and a secondary polar solvent in the foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily.
3. Polyols and PEGs; and combinations of a polyol and/or PEG with a secondary polar solvent are known as skin penetration enhancers, thus, increasing drug residence in the target area and increasing clinical efficacy, as detailed above.
4. The fact that the composition contains no water, or up to 25% and more preferably up to 10% water minimizes the probability of degradation of water-sensitive active agents. Furthermore, as exemplified herein, a foam containing a polyol and/or PEG with no water at all can be formed in accordance with the composition and process of the present invention. Such compositions ensure high stability of water sensitive active agents.
5. Combining the anti-infective effect of a hygroscopic composition, which acts through a dehydration mechanism, with an additional anti-infective agent, selected from the group of an antibiotic agent, an antibacterial agent, an antifungal agent, an agent that controls yeast, an antiviral agent and an antiparasitic agent, that acts through alternate mechanisms results in a synergistic effect and consequently higher success rate of the treatment.
6. The foamable polyol composition in contained in an impermeable pressurized packaging presentation is impermeable and thus, the active agent is not exposed to environmental degradation factors, such as light and oxidating agent during storage.

Thus, in a preferred embodiment of the present invention, the composition includes at least one active agent.

a. a therapeutically effective concentration of an active agent; and
b. about 50% to about 98% of a polar solvent, selected from the group consisting of a polyol and a polyethylene glycol;
c. 0% to about 48% of a secondary polar solvent;
d. about 0.2% to about 5% by weight of a surface-active agent;

e. about 0.01% to about 5% by weight of at least one polymeric agent; and f. a liquefied or compressed gas propellant at a concentration of about 3% to about 25% by weight of the total composition.

In the context of combining a hygroscopic carrier according to the present invention and an anti-infective active agent, a pharmaceutical composition is provided, including:

a. a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7;

b. about 0.2% to about 5% by weight of a surface-active agent;

c. about 0.01% to about 5% by weight of at least one polymeric agent selected from a bioadhesive agent, a gelling agent, a film forming agent and a phase change agent;

d. a therapeutically effective concentration of an anti-infective agent; and e. a liquefied or compressed gas propellant at a concentration of about 3% to about 25% by weight of the total composition.

An exemplary case for the inclusion of an anti-infective agent in a hygroscopic composition is provided herewith. It has been surprisingly discovered that combining an antifungal agent in a hygroscopic composition results in an anti-infective effect on strains that are not supposed to be affected by the said antifungal agent. For example, terbinafine is know to be highly effective against dermatophite pathogens, but not against *candida*. In-vitro studies have revealed, however that terbinafine, dissolved in a hygroscopic carrier, effectively inhibited the spreading of *candida albicans*, while a control preparation, comprising the same concentration of terbinafine in an emulsion base was not effective. Thus, combining an antifungal agent in a hygroscopic composition results in an expansion of the spectrum of infective strains that can benefit form the therapy, and furthermore, in can render an improved effect of such a composition on mixed infections or in infections that are not accurately diagnosed.

Consequently, in another aspect of the present invention, a pharmaceutical composition, which possesses an improved antifungal activity or that possesses an antifungal activity on an expanded spectrum of pathogens, is provided, including:

a. a hygroscopic composition, comprising a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7;

b. an anti-infective agent, selected from the group of an antibiotic agent, an antibacterial agent, an antifungal agent, an agent that controls yeast, an antiviral agent and an antiparasitic agent. Preferably, the anti-infective agent is an antifungal agent, and more preferably the anti-infective agent is terbinafine.

Active Agents

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, wound healing agents and wart removers. As is known to one skilled in the art, in some instances a specific active active agent may have more than one activity, function or effect.

In an embodiment of the present invention, the active agent is an active herbal extract. Suitable active herbal extracts include but are not limited to angelica, anise oil, astragali radix, azalea, benzyl acetate, birch tar oil, bomyl acetate, cacumen biotae, camphor, cantharidin, capsicum, cineole, cinnamon bark, cinnamon leaf, citronella, citroneliol, citronellyl acetate, citronellyl formate, eucalyptus, eugenyl acetate, flos carthami, fructus mori, garlic, geraniol, geranium, geranyl acetate, habanera, isobutyl angelicate, lavender, ledum latifolium, ledum palustre, lemongrass, limonene, linalool, linalyl acetate, methyl anthranilate, methyl cinnamate, mezereum, neem, nerol, nerol acetate, nettle root extract, oleum ricini, oregano, pinenes, .alpha.-pinene, .beta.-pinene, radix angelicae sinesis, radix paenoiae rubra, radix polygoni multiflori, radix rehmanniae, rhizoma pinelliae, rhizoma zingiberis recens, sabadilla, sage, sandalwood oil, saw palmetto extract, semen sesami nigrum, staphysagria, tea tree oil, terpene alcohols, terpene hydrocarbons, terpene esters, terpinene, terpineol, terpinyl acetate and derivatives, esters, salts and mixtures thereof. In an embodiment of the present invention, the active agent is an acaricide. Suitable acaricides include but are not limited to amitraz, flumethrin, fluvalinate and derivatives, esters, salts and mixtures thereof.

In an embodiment of the present invention, the active agent is an age spot and keratoses removing agent. Suitable age spot and keratoses removing agent include but are not limited to hydroxy acids, azelaic acid and other related dicarboxylic acids, retinoids, kojic acid, arbutin, nicotinic, ascorbic acid, hydroquinone and derivatives, esters, salts and mixtures thereof. Certain nonsteroidal anti-inflammatory agents, such as diclofenac are also useful for the treatment of keratoses.

In an embodiment of the present invention, the active agent is an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

In an embodiment of the present invention, the active agent is a local anesthetic. Suitable local anesthetics include but are not limited to benzocaine, benzyl alcohol, bupivacaine, butamben picrate, chloroprocaine, cocaine, dibucaine, dimethisoquin, dyclonine, etidocaine, hexylcaine, ketamine, lidocaine, mepivacaine, phenol, pramoxine, procaine, tetracaine, salicylates and derivatives, esters, salts and mixtures thereof.

In an embodiment of the present invention, the active agent is an antiacne agent. Suitable antiacne agents include but are not limited to N-acetylcysteine, adapalene, azelaic acid, benzoyl peroxide, cholate, clindamycin, deoxycholate, erythromycin, flavinoids, glycolic acid, meclocycline, metronidazol, mupirocin, octopirox, phenoxy ethanol, phenoxy proponol, pyruvic acid, resorcinol, retinoic acid, salicylic acid, scymnol sulfate, sulfacetamide-sulfur, sulfur, tazarotene, tetracycline, tretinoin triclosan and derivatives, esters, salts and mixtures thereof.

In an embodiment of the present invention, the active agent is an antiaging agent. Suitable antiaging agents include but are not limited to sulfur-containing D and L amino acids, alpha-hydroxy acids s, beta-hydroxy acids (e.g. salicylic acid), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate) skin barrier forming agents, melatonin and derivatives, esters, salts and mixtures thereof.

In an embodiment of the present invention, the active agent is an antibiotic. The terms "antibiotic" as used herein shall include, but is not limited to, any substance being destructive to or inhibiting the growth of bacteria or any substance having the capacity to inhibit the growth of or to destroy bacteria. In one or more embodiments, the antibiotic agent is selected from the group consisting of a beta-lactam antibiotic, an aminoglycoside, an ansa-type antibiotic, an anthraquinone, an azole, an antibiotic glycopeptide, a macrolide, an antibiotic nucleoside, an antibiotic peptide, an antibiotic polyene, an antibiotic polyether, an antibiotic quinolone, an antibiotic steroid, a sulfonamide, an antibiotic metal, an oxidizing agent, a periodate, a hypochlorite, a permanganate, a substance that release free radicals and/or active oxygen, a cationic antimicrobial agent, a quaternary ammonium compound, a biguanide, a triguanide, a bisbiguanide, a polymeric biguanide, and analogs, derivatives, salts, ions and complexes thereof.

Suitable antibiotics include but are not limited to amanfadine hydrochloride, amanfadine sulfate, amikacin, amikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

In an embodiment of the present invention, the active agent is an antidandruff agent. Suitable antidandruff agents include but are not limited to aminexil, benzalkonium chloride, benzethonium chloride, 3-bromo-1-chloro-5,5-dimethyl-hydantoin, chloramine B, chloramine T, chlorhexidine, N-chlorosuccinimide, climbazole-, 1,3-dibromo-5,5-dimethylhydantoin, 1,3-dichloro-5,5-dimethyl-hydantoin, betulinic acid, betulonic acid, celastrol, crataegolic acid, cromakalin, cyproterone acetate, dutasteride, finesteride, ibuprofen, ketoconazole, oleanolic acid, phenytoin, picrotone olamine, salicylic acid, selenium sulphides, triclosan, triiodothyronine, ursolic acid, zinc gluconate, zinc omadine, zinc pyrithione and derivatives, esters, salts and mixtures thereof.

In an embodiment of the present invention, the active agent is an antihistamine. Suitable antihistamines include but are not limited to chlorcyclizine, diphenhydramine, mepyramine, methapyrilene, tripelennamine and derivatives, esters, salts and mixtures thereof.

In an embodiment of the present invention, the active agent is an antimycotic Also termed antifungal agent. The terms "antimycotic" and "antifungal" as used herein include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, *dermatophytosis, microsporum, trichophyton* and *epidermophyton* infections, candidiasis, oral candidiasis (thrush), candidiasis of the skin and genital mucous membrane, *candida paronychia*, which inflicts the nail and nail bed and genital and vaginal *candida*, which inflict genitalia and the vagina.

Suitable antimycotics include but are not limited to allylamines, amorolfine, amphotericin B, azole compounds, bifonazole, butoconazole, chloroxine, clotrimazole, ciclopirox olamine, clotrimazole, econazole, elubiol, fenticonazole, fluconazole, flucytosine (5FC), griseofulvin, itraconazole, ketoconazole, mafenide acetate, miconazole, naftifine, natamycin, tolnaftate, nystatin, polyenes, oxiconazole, sulbentine, sulconazole, terbinafine, terconazole, tioconazole, undecylenic acid and derivatives, esters, salts and mixtures thereof.

In an embodiment of the present invention, the active agent is an antipruritic. Suitable antipruritics include but are not limited to menthol, methdilazine, trimeprazine, urea and derivatives, esters, salts and mixtures thereof.

In an embodiment of the present invention, the active agent is an additional antipsoriatic agent. Suitable additional antipsoriatic agents include but are not limited to 6-aminonicotinamide, 6-aminonicotinic acid, 2-aminopyrazinamide, anthralin, 6-carbamoylnicotinamide, 6-chloronicotinamide, 2-carbamoylpyrazinamide, corticosteroids, 6-dimethylaminonicotinamide, dithranol, 6-formylaminonicotinamide, 6-hydroxy nicotinic acid, 6-substituted nicotinamides, 6-substituted nicotinic acid, 2-substituted pyrazinamide, tazarotene, thionicotinamide, trichothecene mycotoxins and derivatives, esters, salts and mixtures thereof.

In an embodiment of the present invention, the active agent is an antirosacea agent. Suitable antirosacea agents include but are not limited to azelaic acid, metronidazole, sulfacetamide and derivatives, esters, salts and mixtures thereof. Certain nonsteroidal anti-inflammatory agents, such as salicylic acid, salycilates, piroxicam and diclofenac are also useful for the treatment of Rosacea.

In an embodiment of the present invention, the active agent is an antiseborrheic agent. Suitable antiseborrheic agents include but are not limited to glycolic acid, salicylic acid, selenium sulfide, zinc pyrithione, a dicarboxylic acid, such as azelaic acid and derivatives, esters, salts and mixtures thereof.

In an embodiment of the present invention, the active agent is an antiviral agent. Suitable antiviral agents include but are not limited to acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

In an embodiment of the present invention, the active agent is a chemotherapeutic agent. Suitable chemotherapeutic agents include but are not limited to daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

In an embodiment of the present invention, the active agent is a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, difluprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

In an embodiment of the present invention, the active agent is a hair growth regulator. Suitable hair growth regulators include but are not limited to N-acetylgalactosamine, N-acetylglucosamine, N-acetylmannosamine, acitretin, aminexil, ascomycin, asiatic acid, azelaic acid, benzalkonium chloride, benzethonium chloride, benzydamine, benzyl nicotinate, benzoyl peroxide, benzyl peroxide, betulinic acid, betulonic acid, calcium pantothenate, celastrol, cepharanthine, chlorpheniramine maleate, clinacycin hydrochloride, crataegolic acid, cromakalin, cyproterone acetate, diazoxide, diphenhydramine hydrochloride, dutasteride, estradiol, ethyl-2-hydroxypropanoate, finasteride, D-fucono-1,5-lactone,furoate, L-galactono-1,4-lactone, D-galactosamine, D-glucaro-1,4-lactone, D-glucosamine-3-sulphate, hinokitiol, hydrocortisone, 2-hydroxypropionic acid, isotretinoin, itraconazole, ketoconazole, latanoprost, 2-methyl propan-2-ol, minocyclin, minoxidil, mipirocin, mometasone, oleanolic acid, panthenol, 1,10-phenanthroline, phenytoin, prednisolone, progesterone, propan-2-ol, pseudoterins, resorcinol, selenium sulfide, tazarotene, triclocarbon, triclosan, triiodothyronine, ursolic acid, zinc pyrithione and derivatives, esters, salts and mixtures thereof.

In an embodiment of the present invention, the active agent is a hormone. Suitable hormones include but are not limited to methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrotestosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogestrel, trimegestone, gestodene, nomegestrol acetate, progesterone, 5a-pregnan-3b,20a-diol sulfate, 5a-pregnan-3b,20b-diol sulfate, 5a-pregnan-3b-ol-20-one, 16,5a-pregnen-3b-ol-20-one, 4-pregnen-20b-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone, progestins and derivatives, esters, salts and mixtures thereof.

In an embodiment of the present invention, the active agent is a hydroxyacid. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllactic acid, mucic acid, phenyllactic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

In an embodiment of the present invention, the active agent is a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratiinization (such as prsoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

In an embodiment of the present invention, the active agent is a lactam. Suitable lactams include but are not limited to L-galactono-1,4-lactam, L-arabino-1,5-lactam, D-fucono-1,5-lactam, D-glucaro-1,4-lactam, D-glucurono-6,3-lactam, 2,5-tri-O-acetyl-D-glucurono-6,3-lactam, 2-acetamido-2-deoxyglucono-1,5-1-actam, 2-acetamido-2-deoxygalactono-1,5-lactam, D-glucaro-1,4:6,3-dilactam-, L-idaro-1,5-lactam, 2,3,5,tri-O-acetyl-D-glucaro-1,4-lactam, 2,5-di-O-acetyl-D-glucaro-1,4:6,3-dilactam, D-glucaro-1,5-lactam methyl ester, 2-propionoamide-2-deoxyglucaro-1,5-lactam and derivatives, esters, salts and mixtures thereof.

In an embodiment of the present invention, the active agent is a non-steroidal anti-inflammatory agent. Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

In an embodiment of the present invention, the active agent is insecticide. The term "insecticide, is used herein to mean a compound which kills, inhibits the growth of, impeded the proliferation of or repels insects. Insecticides include, for example, agents that can kill lice, flees, ticks, mites, scabies and mousquitos, as well as agents that repel such insects. Suitable insecticides include but are not limited to DDT, lindane, malathion, permethrin, allethrin, biopermethrin, transpermethrin, phenothrin, diethyl-m-toluamide, dimethyl phthalate, piperonyl butoxide, pyrethroids and derivatives, esters, salts and mixtures thereof.

In an embodiment of the present invention, the active agent is a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate(triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoceptor blocker, a prostaglandin, sildenafil, dipyridamole, catecholamine, isoproternol, furosemide, prostaglandin, prostacyclin, enalaprilat, morphine, acepromazine, prazosin (α-blocker), enalapril, Captopril, amlodipine, minoxidil, tadalafil, vardenafil, phenylephrin, etilefein, caffeine, capsaicin, an extract capsicum, *achillea millefolium* (Yarrow), *allium sativum* (garlic), *amoracia rusticana* (horseradish), *berberis vulgaris* (barberry), *cimicifuga racemosa* (black cohosh), *coleus forskholii* (*coleus*), *coptis* (goldenthread), *crataegus* (hawthorn), *eleutherococcus senticosus* (siberian ginseng), *ginkgo biloba* (*ginkgo*), *melissa offiicnalis* (lemon balm), *olea europaea* (olive leaf), *panax ginseng* (Chinese ginseng), *petroselinum crispum* (parsley), *scutellaria baicalensis* (baical skullcap), *tilia europaea* (linden flower), *trigonella foenum-graecum* (fenugreek), *urtica dioica* (nettles), *valeriana officinalis* (valerian), *viburnum* (cramp, bark, black haw), *veratrum viride* (American hellebore), *verbena officinalis* (vervain), *xanthoxylum americanum* (prickly ash), *zingiber officinale* (ginger), *rauwolfia serpentina* (Indian snakeroot), viscum album, wild yam, sasparilla, licorice, damiana, yucca, saw palmetto, gotu kola (*centella asiatica*), yohimbine and salts, hazel nut, brazil nut and walnut, and derivatives, esters, salts and mixtures thereof.

In an embodiment of the present invention, the active agent is a vasoconstrictor. Suitable vasodilators include but are not limited to ephedrine, epinephrine, phenylephrine, angiotensin, vasopressin; an extract *ephedra sinica* (ma huang), *polygonum bistorta* (bistort root), *hamamelis virginiana* (witch hazel), *hydrastis canadensis* (goldenseal), *lycopus virginicus* (bugleweed), *aspidosperma quebracho* (quebracho blanco), *cytisus scoparius* (scotch broom) and cypressand and derivatives, esters, salts and mixtures thereof.

In an embodiment of the present invention, the active agent is a retinoid. Suitable retinoids include but are not limited to retinol, retinal, retinoic acid, all-trans retinoic acid, isotretinoin, tazarotene, adapalene, 13-cis-retinoic acid, acitretin all-trans beta carotene, alpha carotene, lycopene, 9-cis-beta-carotene, lutein and zeaxanthin.

In an embodiment of the present invention, the active agent is a vitamin D analog. Suitable retinoids include but are not limited to calcipotriene, cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10, 19-dihydroercalciol, (24S)-ethylcalciol and (22E)-(24R)-ethyl-22,23-didehydrocalciol. In a preferred embodiment, the vitamin D analog is calcipotriene, which is useful in the treatment of psoriasis.

In an embodiment of the present invention, the active agent is selected from the group consisting of an immunosuppressants and immunoregulating agents. Suitable immunosuppressants and immunoregulating agents include but are not limited to cyclic peptides, such as cyclosporine, tacrolimus, tresperimus, pimecrolimus, sirolimus (rapamycin), verolimus, laflunimus, laquinimod, imiquimod derivatives, esters, salts and mixtures thereof. In one or more embodiments, the immunomodulator is a calcineurin Inhibitor.

In an embodiment of the present invention, the active agent is a wart remover. Suitable wart removers include but are not limited to imiquimod, podophyllotoxin and derivatives, esters, salts and mixtures thereof.

In an embodiment of the present invention, the active agent is a photodynamic therapy (PDT) agent. Suitable PDT agents include but are not limited to modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitiser precursors, such as aminolevulinic acid and derivatives, esters, salts and mixtures thereof.

In an embodiment of the present invention, the active agent is an antioxidant or a radical scavenger. Suitable antioxidants and radical scavengers agents include but are not limited to ascorbic acid, ascorbyl esters of fatty acids, magnesium ascorbyl phosphate, sodium ascorbyl phosphate, ascorbyl sorbate, tocopherol, tocopheryl sorbate, tocopheryl acetate, butylated hydroxy benzoic acid, 6-hydroxy-2,5,7,8-tetramethylchroman-2-carboxylic acid, gallic acid, propyl gallate, uric acid, sorbic acid, lipoic acid, diethylhydroxylamine, amino-guanidine, glutathione, dihydroxy fumaric acid, lycine pidolate, arginine pilorate, nordihydroguaiaretic acid, bioflavonoids, curcumin, lysine, methionine, proline, superoxide dismutase, silymarin, tea extracts, grape skin/seed extracts, melanin, and polyunsaturated oils, containing omega-3 and omega-6 fatty acids (e.g., linoleic and linolenic acid, gamma-linoleic acid, eicosapentaenoic acid and docosahexaenoic acid and derivatives, esters, salts and mixtures thereof.

In an embodiment of the present invention, the active agent is a self-tanning agent, such as dihydroxyacetone.

In an embodiment of the present invention, the active agent is an agent, capable of treating hyperhidrosis. Suitable hyperhidrosis agents include but are not limited to anticholinergic drugs, boric acid, tannic acid, resorcinol, potassium permanganate, formaldehyde, glutaraldehyde, methenamine, a Lewis acid, aluminum chloride, aluminum chlorohydrates, zirconium chlorohydrates, aluminum-zirconium-Glycine (AZG) complex, aluminum hydroxybromide, a glycopyrrolate compound, a 5-alpha-reductase inhibitor, finasteride, epristeride, flutamide, spironolactone, saw palmetto extract, cholestan-3-one, a mono- and dicarboxylic acid having 4 to 18 carbon atoms, botulinum toxin, a 5-HT2C receptor antagonist, a 5-HT2C receptor antagonist, ketanserin, ritanserin, mianserin, mesulergine, cyproheptadine, fluoxetine, mirtazapine, olanzapine and ziprasidone.

In an embodiment of the present invention, the active agent is a sunscreen agent. Suitable sunscreen agents include but are not limited to titanium dioxide, zinc oxide, zirconium oxide, iron oxide, p-aminobenzoic acid and its derivatives (ethyl, isobutyl, glyceryl esters; p-dimethylaminobenzoic acid); anthranilic acid derivatives (i.e., o-amino-benzoates, methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid, o- and p-hydroxybiphenyldisulfonates, coumarin derivatives (7-hydroxy, 7-methyl, 3-phenyl), diazoles (2-acetyl-3-bromoindazole, phenyl benzoxazole, methyl naphthoxazole, quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

In an embodiment of the present invention, the active agent is a figure-forming agent and an agent, capable of treating cellulite. Suitable such agents include but are not limited to baldderwack extract, butcher's, broom, cayenne, dandelion, red clover, ginkgo biloba, horse chestnut, witch hazel and borage oil, caffeic acid, nicotinic acid, theophiline and pentoxyphilline and salts and derivatives thereof.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability it is preferred that the composition is substantially non-aqueous. The term "substantially non-aqueous" is intended to indicate that the composition has a water content below about 5%, preferably below about 2%, such as below about 1.5%.

Fields of Applications

The foamable carrier of the present invention is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition of the present invention is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present invention is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present invention, the composition is useful for the treatment of an infection. In one or more embodiments, the composition is suitable for the treatment of an infectiion, selected from the group of a bacterial infection, a fungal infection, a yeast infection, a viral infection and a parasitic infection.

In an embodiment of the present invention, the composition is useful for the treatment of wound, ulcer and burn. This use is particularly important since the composition of the present invention creates a thin, semi-occlusive layer, which coats the damaged tissue, while allowing exudates to be released from the tissue.

The composition of the present invention is also suitable for administering a hormone to the skin or to a mucosal membrane or to a body cavity, in order to deliver the hormone into the tissue of the target organ, in any disorder that responds to treatment with a hormone.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

The invention is described with reference to the following examples. This invention is not limited to these examples and experiments. Many variations will suggest themselves and are within the full intended scope of the appended claims.

Example 1

Foamable Carriers Containing Polyols

| Ingredient | TECH PG-014 % W/W | TECH PG-015 % W/W | TECH PG-016 % W/W |
|---|---|---|---|
| Propylene glycol (PG) | 82.00 | 92.00 | 60.00 |
| Laureth-4 | 2.00 | 2.00 | 2.00 |
| Glyceryl stearate and PEG-100 stearate (Simulsol 165) | 4.00 | 4.00 | 3.00 |
| PEG 4000 | 10.00 | | |
| Glycerin anhydrous | | | 33.00 |
| Hydroxypropylcellulose (Klucel EF) | 2.00 | 2.00 | 2.00 |
| Total | 100.00 | 100.00 | 100.00 |
| Foam quality | Good | Good | Good |
| Shakability | Shakable | Shakable | Shakable |

Notes:
The compositions are substantially non-aqueous
Composition TECH PG-015 contains the minimum number of components that constitute a foamable composition, which upon release from an aerosol pressurized container affords foam of Good or Excellent quality. It contains a diol (PG), a polymeric agent (Klucel EF), and a non-ionic surface active agent (PEG-100 stearate and Laureth 4)
Composition TECH PG-014 demonstrates that the addition of 10% PEG (secondary polar solvent) maintains Good foam quality.
Composition TECH PG-016 demonstrates that a mixture of two polyols (PG and glycerin maintains Good foam quality. This composition possesses high skin hydration effect.
The liquefied or gas propellant can be added at a concentration of about 3% to about 25%.

Example 2

Foamable Carriers Containing Polyols

| Ingredient | TECH PG-021 % W/W | TECH PG-024 % W/W | TECH PG-025 % W/W |
|---|---|---|---|
| Propylene glycol (PG) | 91.00 | 58.00 | 43.00 |
| Stearyl alcohol | 2.00 | 1.00 | 1.00 |
| Laureth-4 | 2.00 | 2.00 | 2.00 |
| Glyceryl stearate and PEG-100 stearate (Simulsol 165) | 3.00 | 3.00 | 3.00 |
| Glycerin | | 33.00 | 33.00 |
| Hydroxypropylcellulose (Klucel EF) | 2.00 | 3.00 | 3.00 |
| Dimethyl isosorbide (DMI) | | | 15.00 |
| Total | 100.00 | 100.00 | 100.00 |
| Foam quality | Excellent | Excellent | Excellent |
| Shakability | Shakable | Shakable | Shakable |

The following procedure was employed when the compositions of Example 2 were produced.
Step 1: Preparation of Phase A
1. Heat Propylene glycol and stearyl alcohol to 80-85° C.
2. Add Klucel while mixing.
3. Cool to 70-75° C. Add all other ingredients while mixing. Agitation continues until solution uniformity is reached
4. Cool solution to 30° C. whith moderate mixing.

Step 2: Canisters Filling and Crimping
1. Each aerosol canister 35×70 mm is filled with 30±5% g of the composition
2. Each canister was closed with an aerosol valve, using a vacuum crimping machine.

Step 3: Pressurizing
Propellant (mix of propane, butane and isobutane) was added to each of the canisters
Notes:
Composition TECH PG-021, 24 and 25 demonstrates that the addition of 1-2% stearyl alcohol (foam adjuvant) facilitates the formation of foam with Excellent quality. Substituting Stearyl alcohol with stearic acid results in an excellent foam too.
Composition TECH PG-025 demonstrates that the addition of 15% DMI (foam adjuvant) facilitates the formation of foam with Excellent quality. This composition possesses high skin penetration enhancing properties.
The liquefied or gas propellant can be added at a concentration of about 3% to about 25%.

Example 3

Foamable Carriers Containing Polyols

| Ingredient | TECH PG-026 % W/W | TECH PG-027 % W/W | TECH PG-028 % W/W |
|---|---|---|---|
| Stearyl alcohol | 2.00 | 1.00 | 1.00 |
| Propylene glycol (PG) | 76.00 | 46.00 | 78.00 |
| Laureth-4 | 2.00 | 2.00 | 2.00 |
| Glyceryl stearate (and) PEG-100 stearate (Simulsol 165) | | 1.50 | |
| Glycerin anhydrous | | 33.00 | |
| Hydroxypropylcellulose (Klucel EF) | 2.00 | 1.50 | 1.50 |
| Dimethyl isosorbide (DMI) | 15.00 | 15.00 | 15.00 |
| Glyceryl stearate | 1.00 | | 1.00 |
| Ceteareth-6 (and) stearyl alcohol (Macrogol cetostearyl ether) | 2.00 | | 1.50 |
| Total | 100.00 | 100.00 | 100.00 |
| Foam quality | Excellent | Excellent | Excellent |

Notes:
Composition TECH PG-027 demonstrates that a mixture of two polyols (PG and glycerin, plus DMI (secondary polar solvent) maintains Exellent foam quality. This composition possesses high skin hydration effect. It further possesses high skin penetration enhancing properties.
The liquefied or gas propellant can be added at a concentration of about 3% to about 25%.

Example 4

Additional Foamable Carriers Containing Polyols, Having Excellent Foam Structure

| Ingredient | TECH-PG 029 % w/w | TECH-PG 030 % w/w | TECH-PG 031 % w/w | TECH-PG 032 % w/w | TECH-PG 033 % w/w |
|---|---|---|---|---|---|
| Propylene Glycol | 91.0 | 58.0 | 43.0 | 46.0 | 78.0 |
| Stearyl Alcohol | 2.0 | 1.0 | 1.0 | 1.0 | 1.0 |
| Glycerin | — | 33.0 | 33.0 | 33.0 | — |
| Klucel EF | 2.0 | 3.0 | 3.0 | 1.5 | 1.5 |
| Laureth-4 | 2.0 | 2.0 | 2.0 | 2.0 | 2.0 |
| Simulsol 165 | 3.0 | 3.0 | 3.0 | 1.5 | — |
| Dimethyl Isosorbide | — | — | 15.0 | 15.0 | 15.0 |
| Macrogol Cetostearyl Ether | — | — | — | — | 1.5 |
| Glyceryl Stearate | — | — | — | — | 1.0 |

Example 5

Foamable Polyols Compositions, Containing Steroid Drugs

The following steroids were included in formulations were included in formulations TECH 30, 31 and 33: bethamethasone valerate 0.12%, clobetasol propionate 0.05%, bethamethasone dipropionate 0.05%, fluocinolone acetonide 0.025%, hydrocortison acetate 0.5% and hydrocortison butyrate 0.1%. All samples were stored at 50° C. for 4 weeks, in order to assess their stability. The following table provides the results of this short-term stability study, which indicated high compatibility between the polyol composition and the steroid drugs, which are known to be temperature-sensitive.

| | % Degradation after 4 weeks at 50° C. | |
|---|---|---|
| | TECH-PG 032 | TECH-PG 033 |
| Bethamethasone Valerate 0.12% | 1.8% | 1.7% |
| Clobetasol Propionate 0.05% | 4.2% | 5.0% |
| Bethamethasone Dipropionate 0.05% | 0 | 0 |
| Fluocinolone Acetonide 0.025% | 1.3% | 1.7% |
| Hydrocortison Acetate 0.5% | 1.6% | 2.1% |
| Hydrocortison Butyrate 0.1% | 2.6% | 2.8 |

Example 6

Foamable Polyol Pharmaceutical Composition Comprising a Combination of Betamethasone Dipropionate and Calcipotriol

| Ingredient | FXCLB1 % W/W | FXCLB2 % W/W |
|---|---|---|
| Propylene glycol | 90.945 | 77.945 |
| Stearyl alcohol | 2.00 | 1.00 |
| Klucel EF | 2.00 | 1.50 |
| Laureth-4 | 2.00 | 2.00 |
| Simulsol 165 | 3.00 | |
| Macrogol Cetostearyl Ether | | 1.50 |
| Glyceryl Stearate | | 1.00 |
| Dimethyl isosorbide | | 15.00 |
| Calcipotriol | 0.005 | 0.005 |
| Betamethasone Dipropionate | 0.05 | 0.05 |

Notes:
Composition FXCLB1 and FXCLB2 contain two active agents (a corticosteroid and a vitamin D derivative, which are known of exert a synergistic therapeutic effect in psoriasis. These compositions contribute to enhanced skin penetration of the active agents.

The liquefied or gas propellant can be added at a concentration of about 3% to about 25%.

Example 7

Foamable Polyol Pharmaceutical Composition Comprising Acyclovir

| Ingredient | % W/W |
|---|---|
| Acyclovir | 5.00 |
| Propylene Glycol | 43.70 |
| Stearyl Alcohol | 0.95 |
| Glycerin | 31.35 |
| Hydroxypropyl cellulose | 1.43 |
| Laureth-4 | 1.90 |
| Glyceryl Monostearate/PEG 100 Stearate | 1.43 |
| Dimethyl Isosorbide | 14.25 |

Notes:
The composition contains acyclovir, which is not fully soluble in the plyol and DMI mixture. However, due to the unique composition, the acyclovir does not readily precipitate and does not undergo caking Furthermore, thanks to the low viscosity of the composition, upon shaking the active agent readily re-disperses in the composition, resulting in full formulation uniformity.

The combination of polyols and dimethyl isosorbide contributes to enhanced skin bioavailability of the active agent.

The liquefied or gas propellant can be added at a concentration of about 3% to about 25%.

Example 8

Foamable Compositions Containing Polyethylene Glycol

| | % w/w | % w/w | % w/w | % w/w | % w/w | % w/w | % w/w |
|---|---|---|---|---|---|---|---|
| PEG400 | 87.50 | 91.50 | 87.50 | 89.50 | 87.50 | 87.50 | 87.50 |
| Klucel MX (hydroxypropyl cellulose) | 0.50 | 0 | 0.50 | 0 | 0.50 | 0 | 0.50 |
| Klucel LF (hydroxypropyl cellulose) | 0 | 0.50 | 0 | 0.50 | 0 | 0.50 | 0 |
| Lipocol C2 (POE (2) cetyl ether) | 2.00 | 2.00 | 0 | 0 | 0 | 0 | 0 |
| Myrj 52 | 0 | 0 | 2.00 | 2.00 | 0 | 0 | 0 |
| Steareth-2 | 0 | 0 | 0 | 0 | 2.00 | 2.00 | 0 |
| Dermofeel G10L (Polyglyceryl-10 Laurate) | 0 | 0 | 0 | 0 | 0 | 0 | 2.00 |
| Propellant | 10 | 6 | 10 | 8 | 10 | 10 | 10 |
| Density | 0.060 | 0.063 | 0.063 | 0.055 | 0.052 | 0.050 | 0.075 |

Notes:
The liquefied or gas propellant can be added at a concentration of about 3% to about 25%.

The foams of this example have a non-ionic surface active agent at a concentration of 2%. Total amounts of surface active agent foam adjuvant and polymeric agent is in the range of 2.5%.

The compositions are useful as carriers of various active therapeutic active agents.

Example 9

Foamable Hygroscopic Compositions, Containing Mupirocin

The following table exemplifies the use of PEG as a hygroscopic substance, which also serves as an effective solvent for Mupirocin, which is practically insoluble in mineral oil and other commonly used ointment solvents. Note that Mupirocin is incompatible with most solvents and thus, a foam comprising PEG as the sole solvent is highly valuable.

| | % w/w | % w/w | % w/w |
|---|---|---|---|
| Mupirocin | 2.00 | 2.00 | 2.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |
| Polyglyceryl-10 Laurate | | | 2.00 |
| Propellant (Propane/butane)* | 6.0 | 6.0 | 6.0 |
| Density | 0.060 | 0.060 | 0.062 |

Notes:
The liquefied or gas propellant can be added at a concentration of about 3% to about 25%.

The foams of this example have a non-ionic surface active agent at a concentration of 2%. Total amounts of surface active agent foam adjuvant and polymeric agent is in the range of 2.5% (w/w).

Example 10

Foamable Hygroscopic Compositions, Containing Terbinafine

The following table exemplifies the use of PEG as a hygroscopic substance, which also serves as an effective solvent for terbinafine, which is hard to dissolve in common formulation excipients.

| | % w/w | % w/w | % w/w |
|---|---|---|---|
| Terbinafine | 2.00 | 2.00 | 6.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |

-continued

|  | % w/w | % w/w | % w/w |
|---|---|---|---|
| Polyglyceryl-10 Laurate |  |  | 2.00 |
| Propellant (Propane/butane)* | 6.0 | 6.0 | 6.0 |
| Density | 0.060 | 0.060 | 0.062 |

Example 11

Comparative In-Vitro Activity of a Hygroscopic Composition Containing Terbinafine A comparative in-vitro study was set to evaluate the effect of Composition A, consisting of 2% terbinafine, 95.3% gr. polyethylene glycol, 0.5% hydroxypropyl cellulose and 2.2% steareth-2, in comparison with Composition B (an oil in water emulsion containing 2% terbinafine) and Composition C a commercial 1% bifonazole cream.

Three fungal strains (*microsporum canis*, *trichophyton mentagrophytes* and *trichophyton rubrum*) and one yeast (*candida albicans*) were seeded in the center of a Petri dish, and then, were surrounded by a film containing each of the compositions, using a swab, soaked with each of the compositions. The proliferation and spreading of the microorganisms was followed up for 14 day by visual and photographic observations.

Figure 1B:
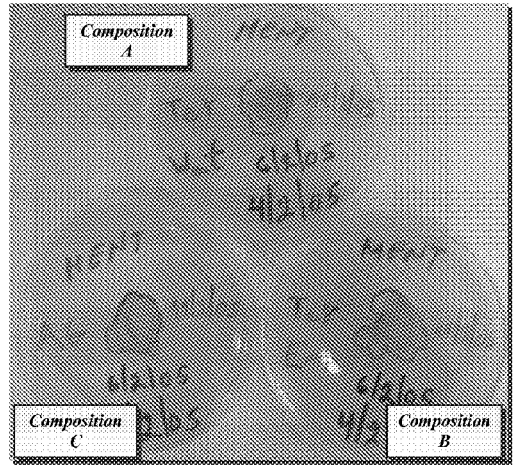
Figure 1C:
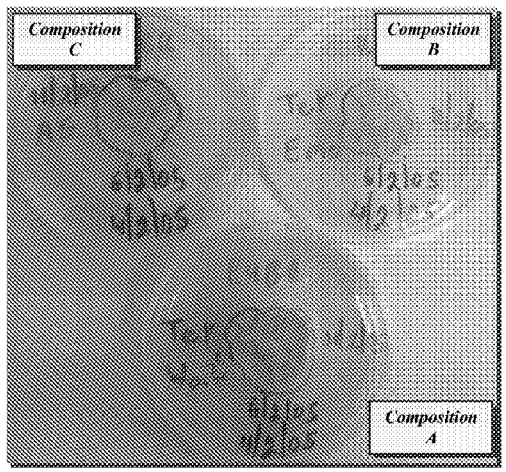
Figure 1D:
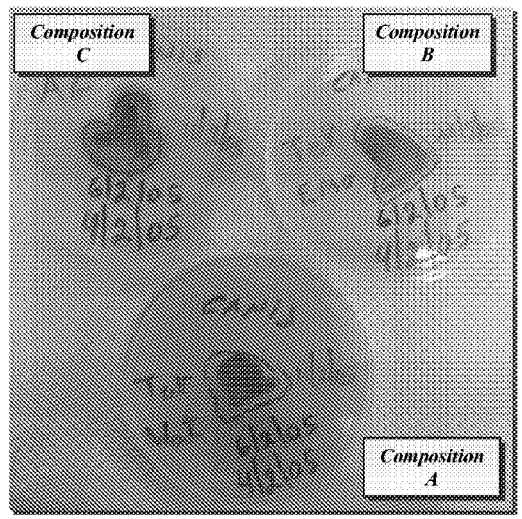

As shown in FIG. 1, Composition A inhibited the proliferation and spreading of all the fungal and yeast strains effectively. By contrast, both Compositions B and C failed to inhibit the growth of *candida*. Composition C was also ineffective in the inhibition of *microsporum canis* and *Trichophyton rubrum*.

Example 12

Foamable Hygroscopic Composition Containing Dimethyl Isosorbide

|  | % w/w | % w/w | % w/w | % w/w |
|---|---|---|---|---|
| Oleyl alcohol | 2.50 | — | — | — |
| IPM | 5.00 | 5.00 | 5.00 | — |
| Caprylic/Capric Triglyceride (MCT oil) | 5.00 | 5.00 | 5.00 | 46.00 |
| Epikuron P100 | — | — | — | 10.00 |
| PPG-15 stearyl ether | — | — | — | 2.00 |
| Sorbitane stearate | 8.00 | 8.00 | 8.00 | 2.00 |
| Glyceril monostearate | — | 1.00 | 1.00 | 1.00 |
| Stearyl alcohol | — | 5.00 | 5.00 | — |
| Cetostearyl alcohol | 8.00 | — | — | — |
| Klucel MF | — | 0.50 | — | — |
| PVP K-90 | — | — | — | 0.50 |
| Sisterna SP50 | 5.00 | 8.00 | 8.00 | — |
| Propylene glycol | 2.50 | — | — | — |
| DMI | 55.50 | 59.00 | 59.50 | 20.00 |
| Water pure | — | — | — | 10.00 |
| Phenonip | 0.50 | 0.50 | 0.50 | 0.50 |
| Propellant | 8.00 | 8.00 | 8.00 | 8.00 |

Example 13

Hygroscopic Antifungal Compositions

|  | Ointment Type | | | Lacquer Type | | |
|---|---|---|---|---|---|---|
|  | % w/w | % w/w | % w/w | % w/w | % w/w | % w/w |
| PEG 400 | 92.00 | 92.00 | 93.00 | — | 54.00 | 46.00 |
| PEG 4000 | 6.00 | — | — | — | — | — |
| PEG 6000 | — | 6.00 | 6.00 | — | 10.00 | 8.00 |
| Ethyl acetate/Isopropanol | — | — | — | 30.00 | 30.00 | 30.00 |
| Urea | — | — | — | — | — | 10.00 |
| Terbinafine | 2.00 | 2.00 | — | 2.00 | 4.00 | — |
| Ciclopirox | — | — | 1.00 | — | — | 4.00 |

The lacquer type compositions are suitable for the treatment of infected cornified tissues, and particularly the nail.

Example 14

Comparison between Polyethylene-Based Foamable Compositions with and without Gelling Agent The compositions of the test articles are provided in the following table. All foams were dispensed on a warm surface (38° C.), and the time to full collapse of the foam was measured. As shown in the table, it has been strikingly demonstrated that foam compositions without a gelling agent exhibit a 100% breakdown within 30 seconds, while foams containing gelling agent remained, with and without surfactant, were stable for several minutes. This is relevant from the usability point of view, since a foam that is unstable at skin temperature cannot be applied to large areas affectively.

|  | Formulations without gelling agent | | | | Formulation with gelling agent | |
|---|---|---|---|---|---|---|
|  | PG33 % w/w | PG34 % w/w | PG35 % w/w | PG36 % w/w | TEC49 % w/w | PG29 % w/w |
| PEG 400 | 87.25 | 93.00 | 91.00 | 92.00 | 90.50 | 93.50 |
| Klucel GF (gelling agent) | — | — | — | — | 0.50 | 0.50 |
| Ceteareth-15 | — | — | 2.00 | 1.00 | — | — |
| Emulsiying Wax NF | 1.80 | — | — | — | — | — |
| Steareth-10 | — | 0.40 | — | 0.50 | — | — |
| PEG-40 stearate | 1.35 | — | — | — | — | — |
| Steareth-2 | — | 0.60 | 1.00 | 0.50 | 1.00 | — |
| Span 60 | 2.70 | — | — | — | — | — |
| Polysorbate 60 | 0.90 | — | — | — | — | — |
| Propellant | 6.00 | 6.00 | 6.00 | 6.00 | 8.00 | 6.00 |
| Collapse time (Seconds; 38° C.) | <30 | <30 | <30 | <30 | 240 | >300 |

Example 15

Foamable Hygroscopic Composition Containing Polyethylene Glycol with No Surfactant

|  | % w/w |
| --- | --- |
| PEG 400 | 93.50 |
| Klucel GF | 0.50 |
| Propellant (Butane/propane) | 6.00 |
| Foam quality | E |
| Density | 0.09 |

What is claimed is:

1. A foamable hygroscopic pharmaceutical composition in a pressurized container, the foamable hygroscopic pharmaceutical composition comprising:
   i) a carrier composition comprising:
      a. at least one hygroscopic substance selected from the group consisting of:
      a polyethylene glycol (PEG) and a polyol at a sufficient concentration to provide an Aw value of the hygroscopic pharmaceutical composition of less than 0.9;
      b. about 0.01% to about 5% by weight of the carrier composition of a gelling agent; and
      c. 0% to about 25% by weight of the carrier composition of water; and
   ii) a liquefied or compressed gas propellant;
wherein the foamable hygroscopic pharmaceutical composition forms a breakable foam upon release from the pressurized container; wherein the breakable foam does not immediately collapse upon exposure to skin temperature; and wherein the breakable foam breaks under shear force.

2. The hygroscopic pharmaceutical composition of claim 1, further comprising 0% to about 5% by weight of a surface-active agent; and a therapeutically effective concentration of one or more active agents.

3. A foamable pharmaceutical carrier composition in a pressurized container comprising:
   i) a carrier composition comprising:
      a. about 50% to about 98% by weight of the carrier composition of a polar solvent selected from the group consisting of (1) a polyol and (2) a polyethylene glycol (PEG);
      b. 0% to about 48% by weight of the carrier composition of a secondary polar solvent;
      c. about 0.01% to about 5% by weight of the carrier composition of a gelling agent; and
      d. 0% to about 25% by weight of the carrier composition of water; and
   ii) a liquefied or compressed gas propellant;
wherein the foamable pharmaceutical carrier composition forms a breakable foam upon dispensing from the pressurized container; wherein the breakable foam does not immediately collapse upon exposure to skin temperature; and wherein the breakable foam breaks under shear force.

4. The pharmaceutical composition of claim 3, wherein the gelling agent comprises a cellulose polymer.

5. The pharmaceutical composition of claim 3, wherein the polar solvent is a PEG selected from the group consisting of PEG 200, PEG 300, PEG 400, PEG 600, PEG 1000, PEG 4000, PEG 6000 and PEG 8000.

6. The pharmaceutical composition of claim 3, wherein the composition does not contain a surface-active agent.

7. The pharmaceutical composition of claim 3, further comprising a therapeutically effective concentration of one or more active agents.

8. The pharmaceutical composition of claim 3, wherein the polyol comprises at least one of glycerin, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol, and dibutylene glycol or a mixture of at least two polyols.

9. The pharmaceutical composition of claim 3, wherein the polar solvent comprises a mixture of at least one polyol and at least one PEG.

10. The pharmaceutical composition of claim 3, wherein the pharmaceutical composition is substantially non-aqueous.

11. The pharmaceutical composition of claim 3, wherein the pharmaceutical composition is substantially free of short-chain alcohols.

12. The pharmaceutical composition of claim 3, wherein the pharmaceutical composition forms a stable foam at normal skin temperature for at least about 240 seconds upon release from the pressurized container.

13. The pharmaceutical composition of claim 3, further comprising about 0.2% to about 5% by weight of a surface-active agent.

14. The pharmaceutical composition of claim 13, wherein the surface-active agent comprises a non-ionic surfactant.

15. The pharmaceutical composition of claim 13, wherein the surface-active agent comprises at least one non-ionic surfactant and at least one ionic surfactant.

16. The pharmaceutical composition of claim 15, wherein the ratio of non-ionic surfactant to ionic surfactant is in the range of about 100:1 to about 6:1.

17. The pharmaceutical composition of claim 13, further comprising a hygroscopic substance selected from the group consisting of monosaccharides, disaccharides, oligosaccharides, sugar alcohols, honey and a PEG containing surfactant, wherein the composition can provide an Aw value of less than 0.9.

18. The pharmaceutical composition of claim 17, further comprising a therapeutically effective concentration of one or more active agents.

* * * * *